(12) United States Patent
Wang et al.

(10) Patent No.: US 8,455,454 B2
(45) Date of Patent: Jun. 4, 2013

(54) MIR 204, MIR 211, THEIR ANTI-MIRS, AND THERAPEUTIC USES OF SAME

(75) Inventors: Fei Wang, Bethesda, MD (US); Sheldon Miller, Bethesda, MD (US); Congxiao Zhang, Rockville, MD (US); Arvydas Maminishkis, Washington, DC (US)

(73) Assignee: The United States of America, as represented by the Secretary, Department of Health and Human Services, Washington, DC (US)

( * ) Notice: Subject to any disclaimer, the term of this patent is extended or adjusted under 35 U.S.C. 154(b) by 0 days.

(21) Appl. No.: 13/060,877

(22) PCT Filed: Aug. 26, 2009

(86) PCT No.: PCT/US2009/055000
§ 371 (c)(1),
(2), (4) Date: Apr. 15, 2011

(87) PCT Pub. No.: WO2010/027838
PCT Pub. Date: Mar. 11, 2010

(65) Prior Publication Data
US 2011/0190378 A1  Aug. 4, 2011

Related U.S. Application Data

(60) Provisional application No. 61/092,102, filed on Aug. 27, 2008.

(51) Int. Cl.
*C12N 15/11* (2006.01)
*A61K 48/00* (2006.01)
*C07H 21/02* (2006.01)
*C07H 21/04* (2006.01)

(52) U.S. Cl.
USPC .................................. 514/44 A; 536/24.5

(58) Field of Classification Search
USPC ............................................ 536/23.1, 24.5
See application file for complete search history.

(56) References Cited

U.S. PATENT DOCUMENTS

| 2005/0182005 A1 | 8/2005 | Tuschl et al. |
| 2007/0243132 A1 | 10/2007 | Russell-Jones et al. |
| 2007/0253956 A1 | 11/2007 | Cui et al. |

FOREIGN PATENT DOCUMENTS

WO   WO 2007/081680 A2   7/2007

OTHER PUBLICATIONS

Lagos-Quintana et al. (RNA, 2003 vol. 9(2):175-179).*

(Continued)

*Primary Examiner* — Terra Cotta Gibbs
(74) *Attorney, Agent, or Firm* — Leydig, Voit & Mayer, Ltd.

(57) ABSTRACT

Embodiments of the invention provide methods of preventing or treating detrimental epithelial cell proliferation, loss of epithelial cell differentiation, age-related macular degeneration and/or proliferative vitreal retinopathy in an individual comprising administering to an individual in need thereof an effective amount of miR 204, an effective amount of miR 211, or an effective amount of a mixture of miR 204 and miR 211. A further embodiment of the invention provides a method of facilitating the transport of a substance across an epithelium in an individual comprising administrating to an individual an effective amount of anti-miR 204, an effective amount of anti-miR 211, or an effective amount of a mixture of anti-miR 204 and anti-miR 211. Additional embodiments of the invention include pharmaceutical compositions of miR 204 and/or miR 211 and pharmaceutical compositions of anti-miR 204 and/or anti-miR 211.

16 Claims, 22 Drawing Sheets

OTHER PUBLICATIONS

Lagos-Quintana et al. (Current Biology, 2002 vol. 12:735-739), Supplementary Material.*
Liu et al. (International Journal of Molecular Science, 2008 vol. 9:978-999).*
Agrawal et al., *Microbiol. Molec. Biol. Rev.*, 67 (4), 657-685 (2003).
Bak et al., *RNA*, 14 (3), 432-444 (2008).
Chen et al., *Nucl. Acids Res.*, 33 (22), e190, 1-8 (2005).
Deo et al., *Developmental Dynamics*, 235, 2538-2548 (2006).
Gaur et al., *Cancer Res.*, 67 (6), 2456-2468 (2007).
Gregory et al., *Nat. Cell Biol.*, 10 (5), 593-502 (2008).
Hammond, *Nat. Genet.*, 39 (5), 582-583 (2007).
Huang et al., *Mamm. Genome*, 19, 510-516 (2008).
Jager et al., *N. Engl. J. Med.*, 358 (24), 2606-2617 (2008).
Karali et al., *Invest. Ophthalmol. Vis. Sci.*, 48 (2), 509-515 (2007).
Kumar et al., *Nat. Genet.*, 39 (5), 673-677 (2007).
Lao et al., *Biochem. Biophys. Res. Commun.*, 343, 85-89 (2006).
Letessier et al., *Oncogene*, 26, 298-307 (2007).
Levayer et al., *Nat. Cell Biol.*, 10 (7), 757-759 (2008).
Li et al., *Invest. Ophthalmol. Vis. Sci.*, 48 (12), 5722-5732 (2007).
Li et al., *Invest. Ophthalmol. Vis. Sci.*, 48 (Abstract 5728), 2007.
Lim et al., *Science*, 299 (5612), 1540 (2003).
Livak et al., *Methods*, 25, 402-408 (2001).
Maminishkis et al., *Invest. Ophthalmol. Vis. Sci.*, 47 (8), 3612-3624 (2006).
Miska, *Nat. Cell Biol.*, 10 (5), 501-502 (2008).
Montell et al., *Curr. Opin. Cell Biol.*, 16, 115-118 (2004).
Morello, *Am. J. Health-Syst. Pharm.*, 64 (Suppl. 12), S3-S7 (2007).
Pratt et al., *Molecular Vision*, 14, 1414-1428 (2008).
Ryan et al., *Molecular Vision*, 12, 1175-1184 (2006).
Stark et al., *Pigment Cell*, Abstract PP 21-3, 334 (2008).
Tsonis et al., *Biochem. Biophysical Res. Comm.*, 362, 940-945 (2007).
Vermeulen et al., *RNA*, 13, 723-730 (2007).
Wang et al., *FASEB J.*, 24, 1552-1571 (2010) (with supplementary material).
Wang et al., *Invest. Ophthalmol. Vis. Sci.*, 47(Abstract 2855), 2006.
Wang et al., *Invest. Ophthalmol. Vis. Sci.*, 48 (Abstract 6034), 2006.
Xu et al., *J. Biol. Chem.*, 282 (34), 25053-25066 (2007).
Zavadil et al., *Cells Tissues Organs*, 185 (1-3), 157-161 (2007).
Zhi et al., *Invest. Ophthalmol. Vis. Sci.*, 47 (Abstract 2532), 2007.
Zhi et al., *Invest. Ophthalmol. Vis. Sci.*, 47 (Abstract 4904), 2006.

* cited by examiner

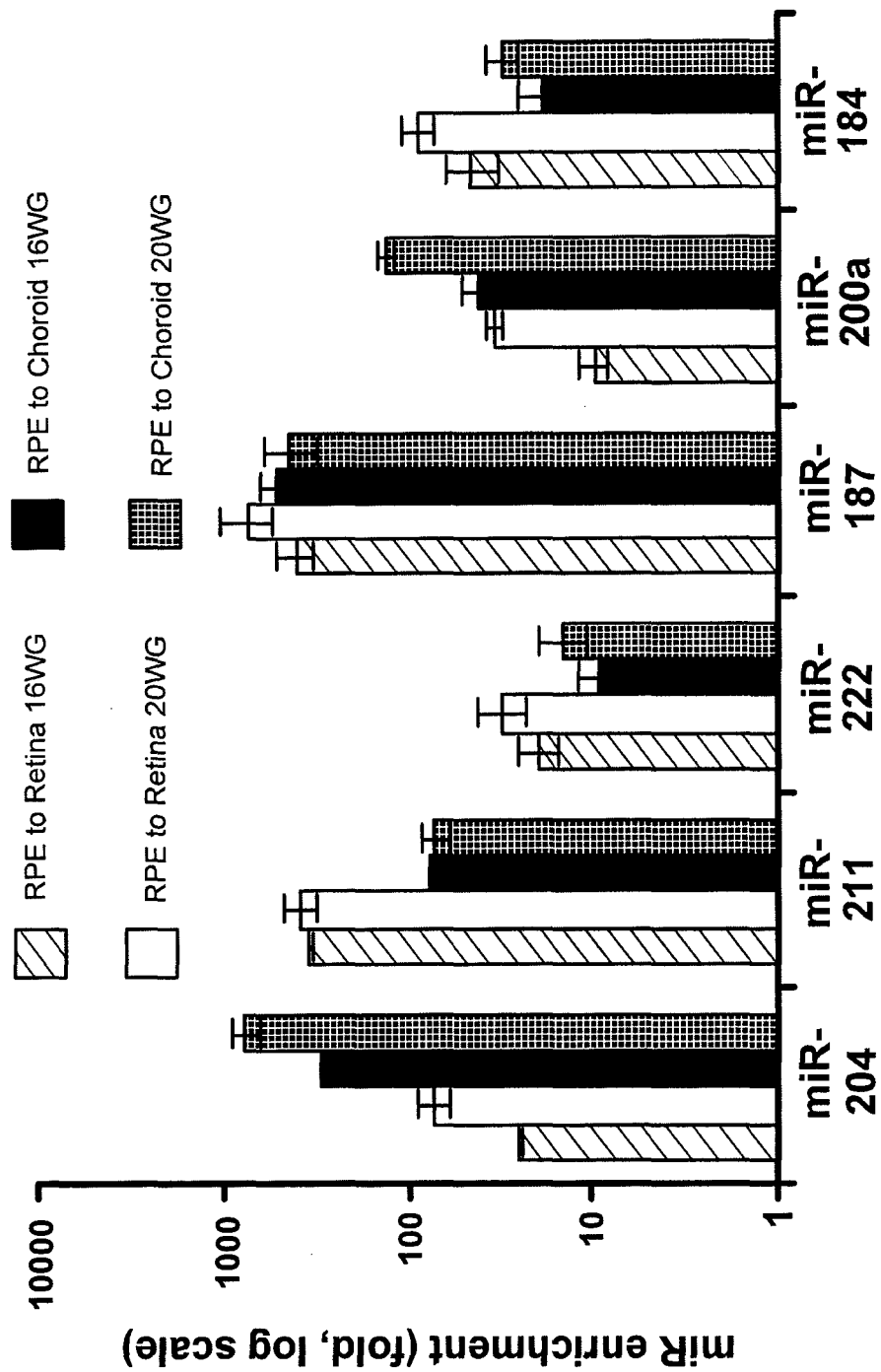

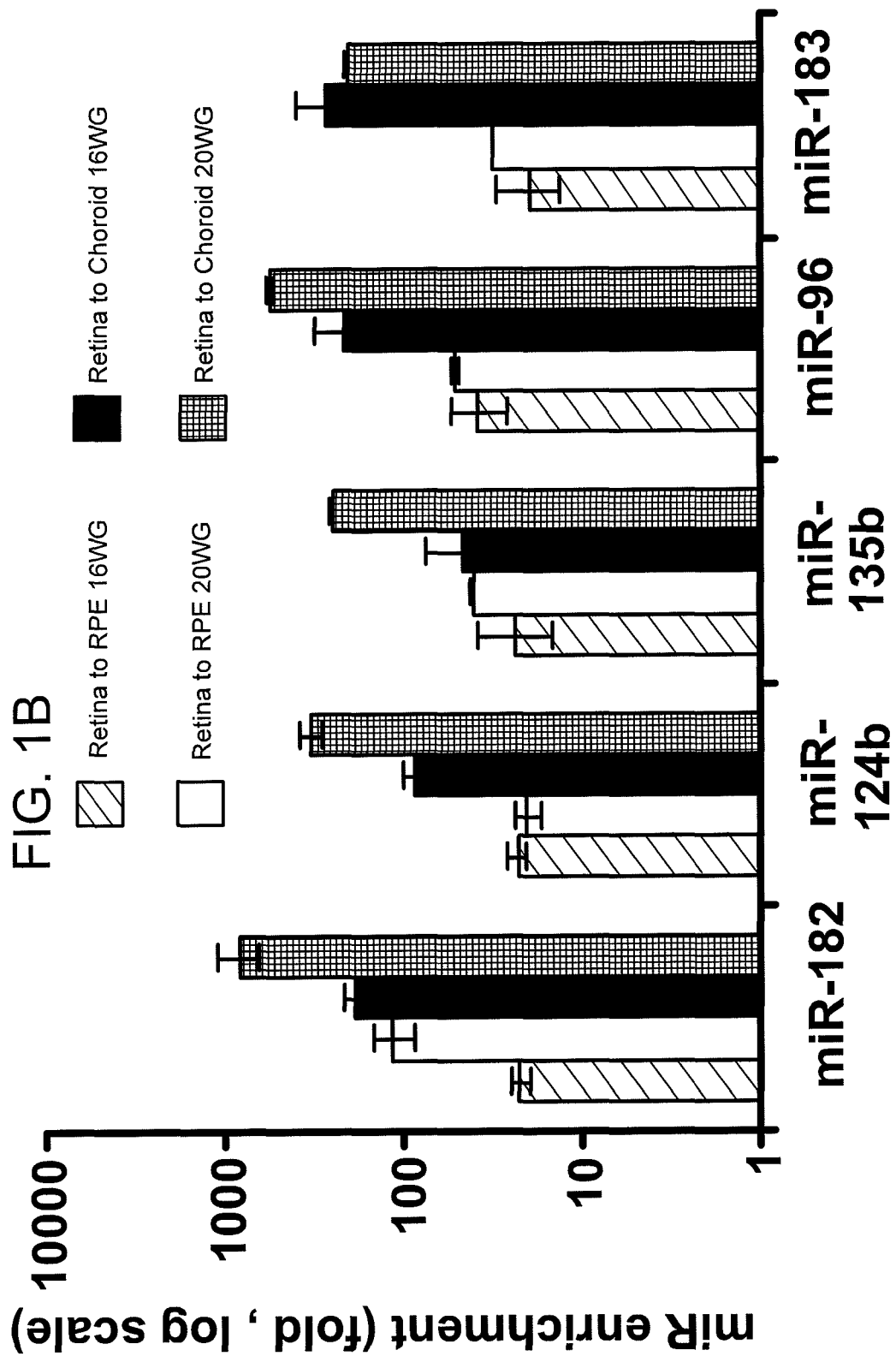

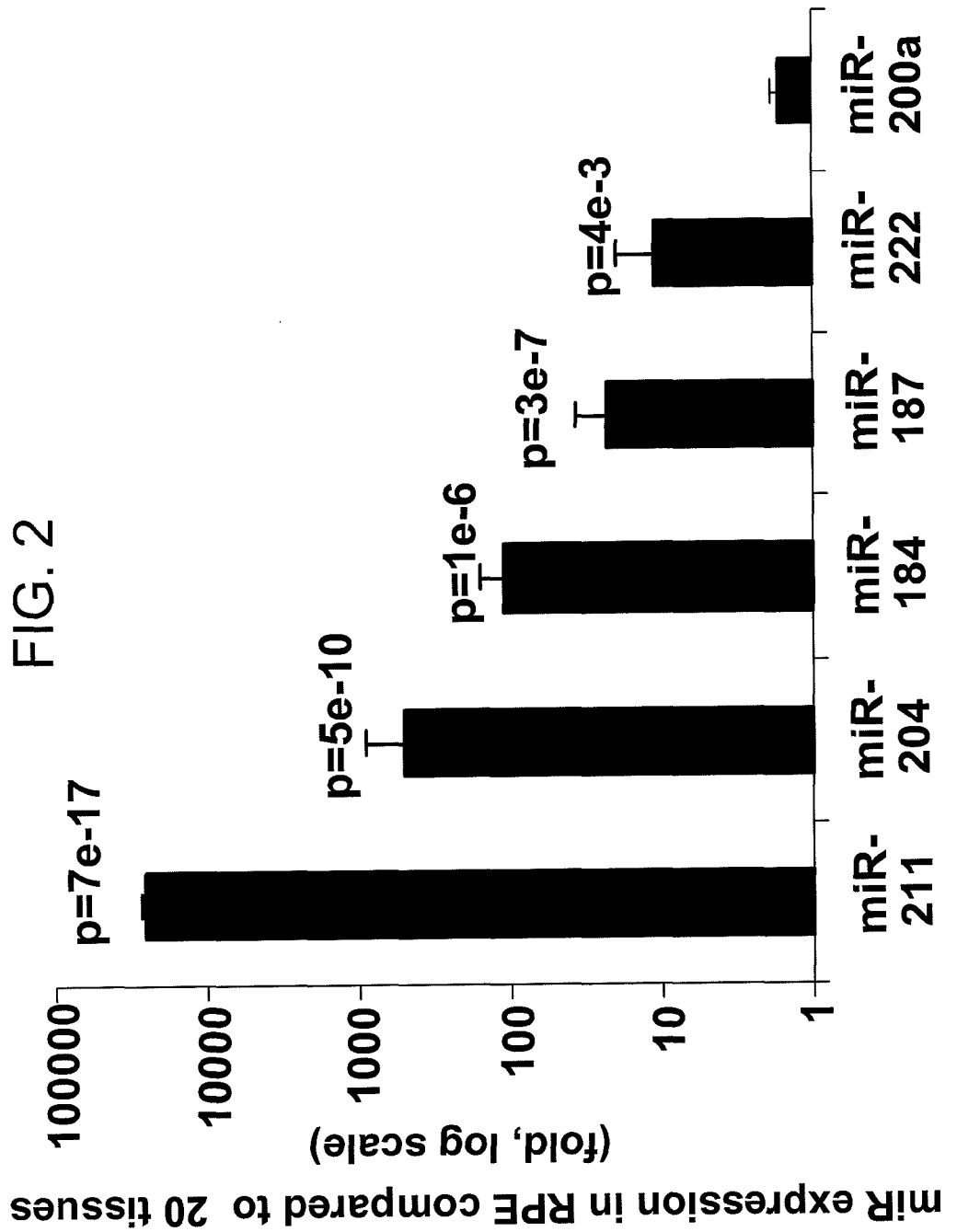

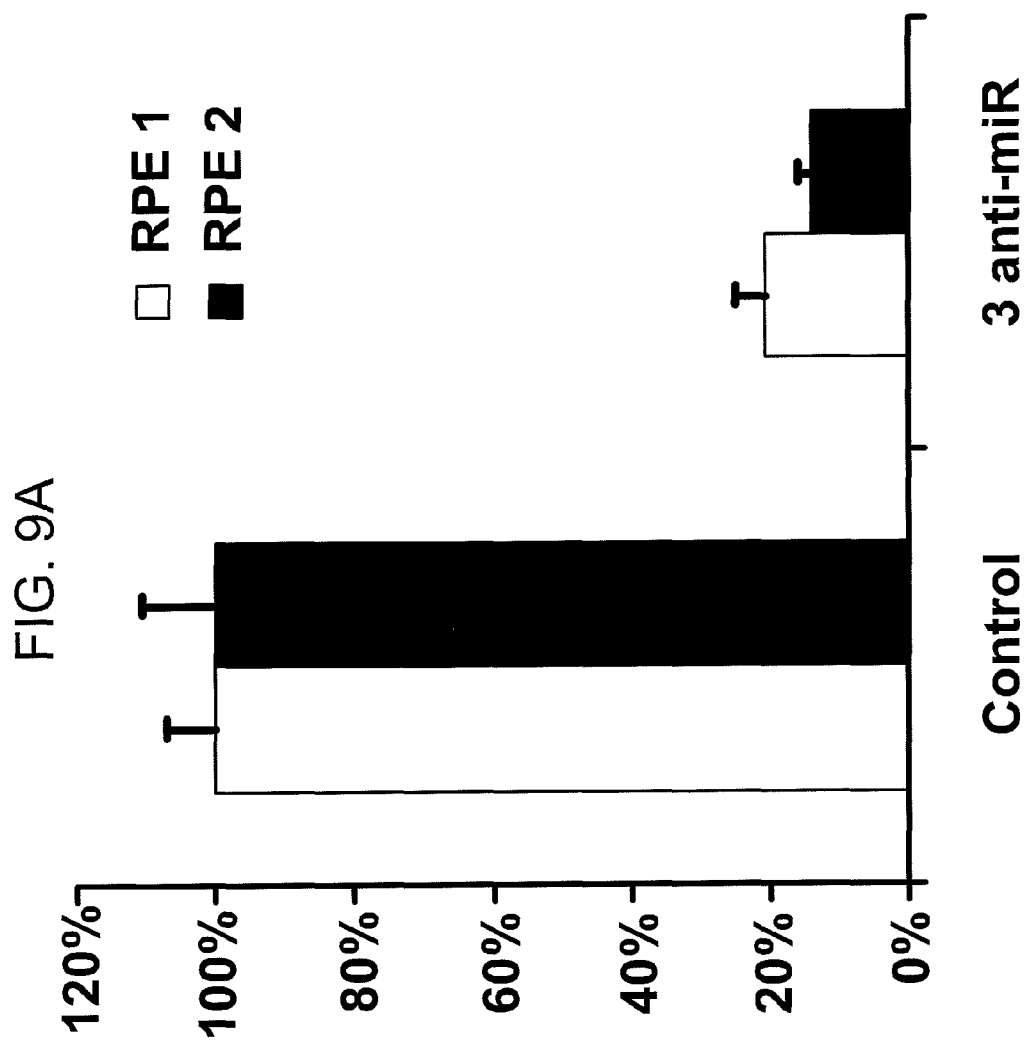

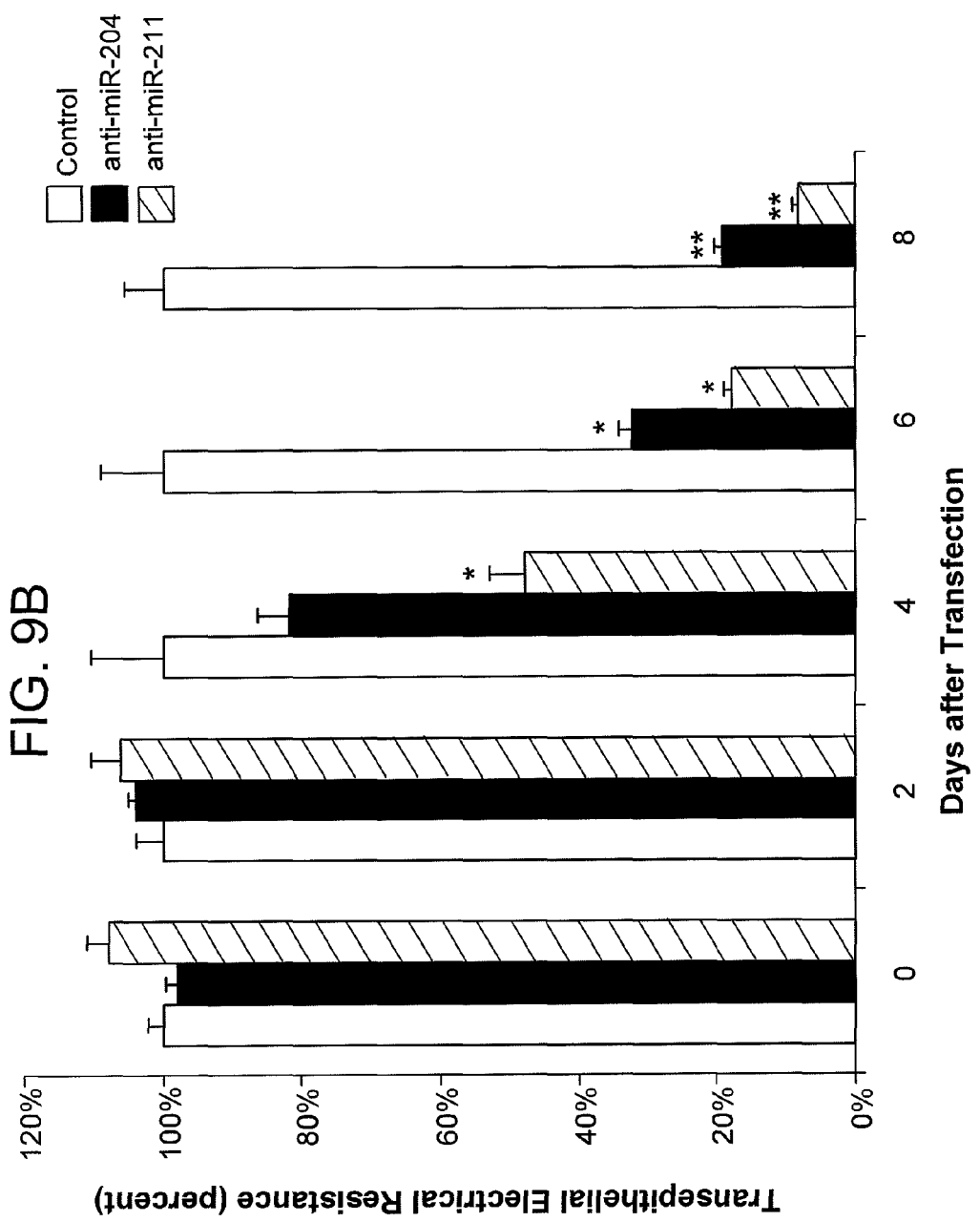

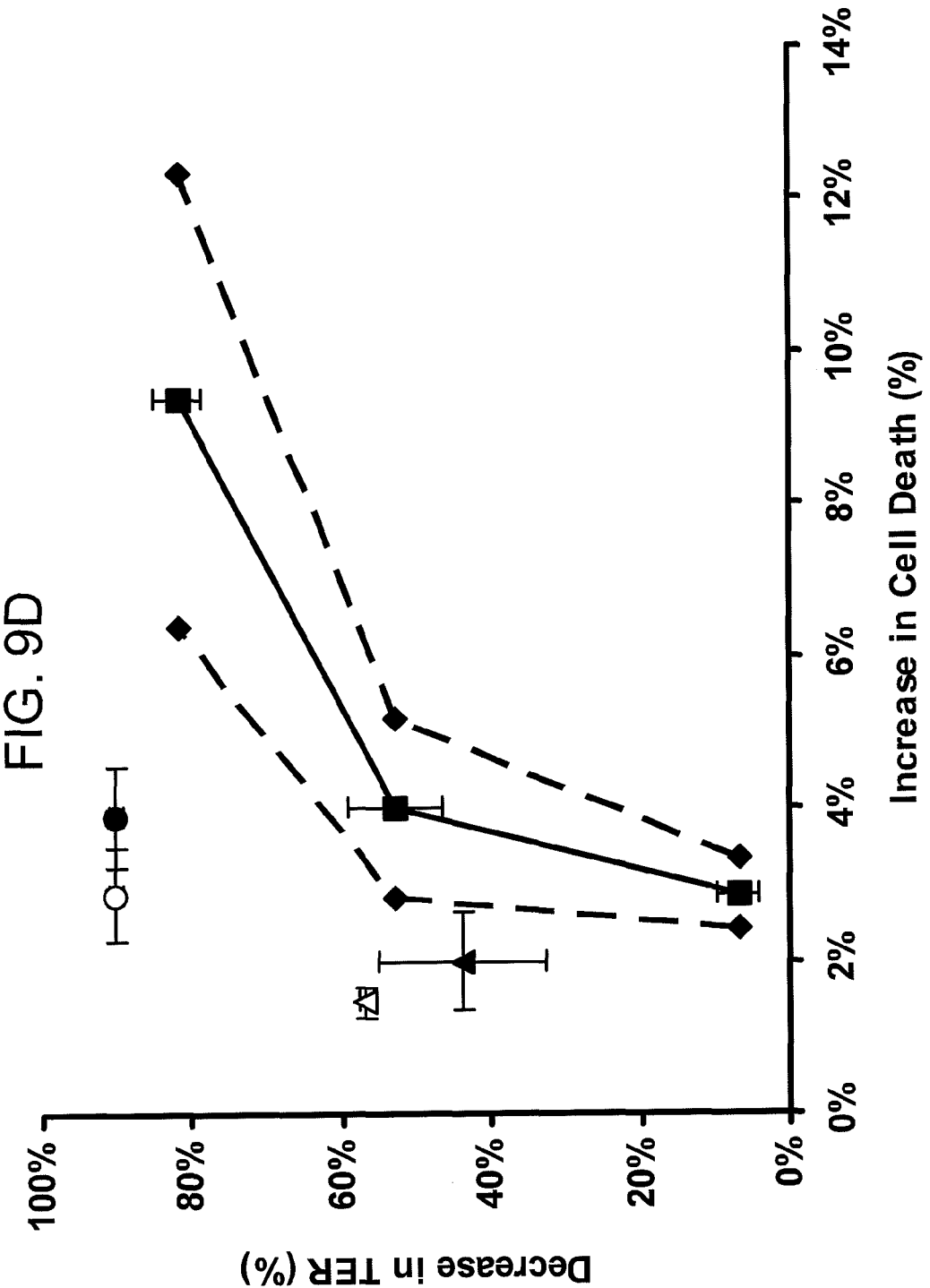

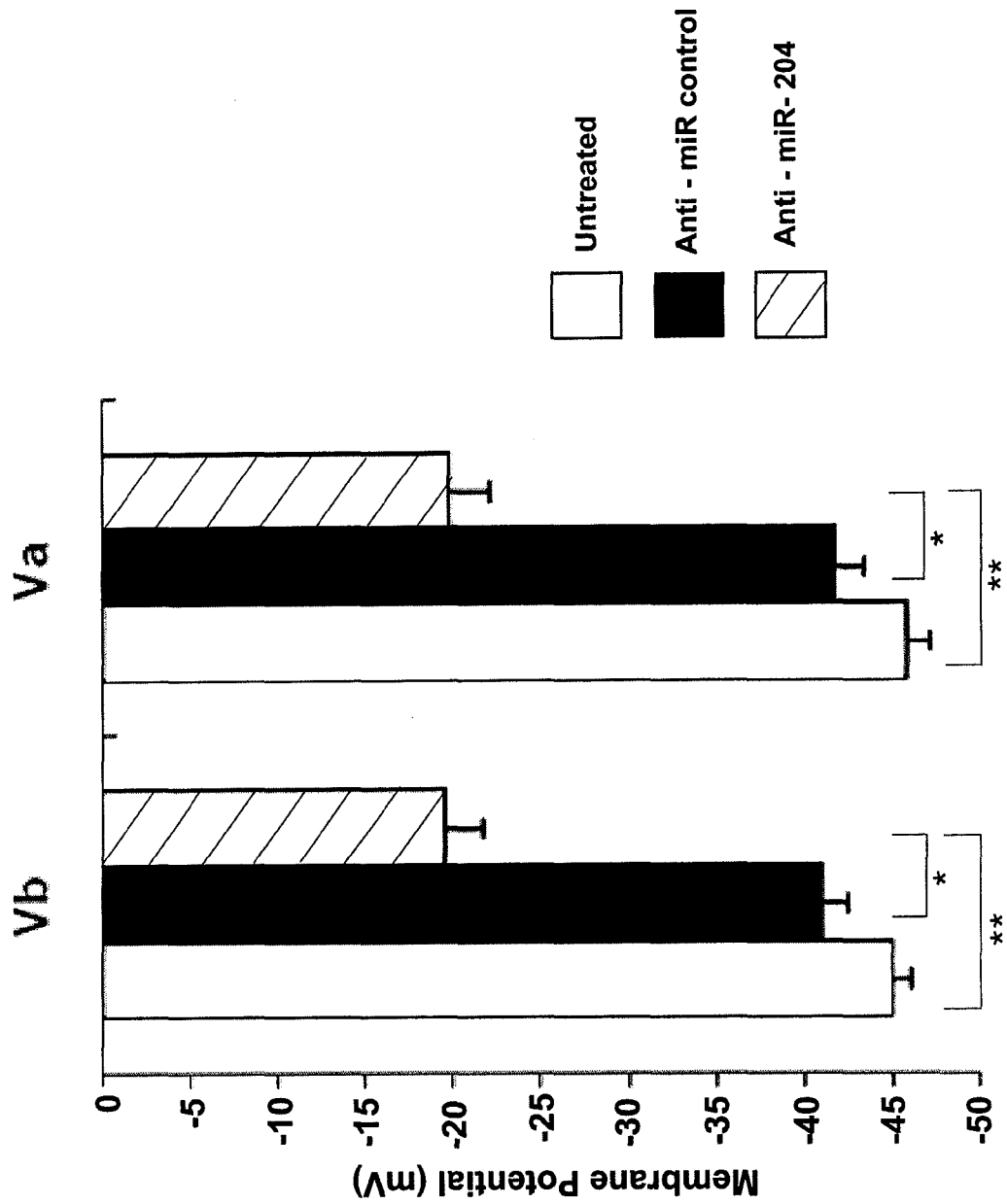

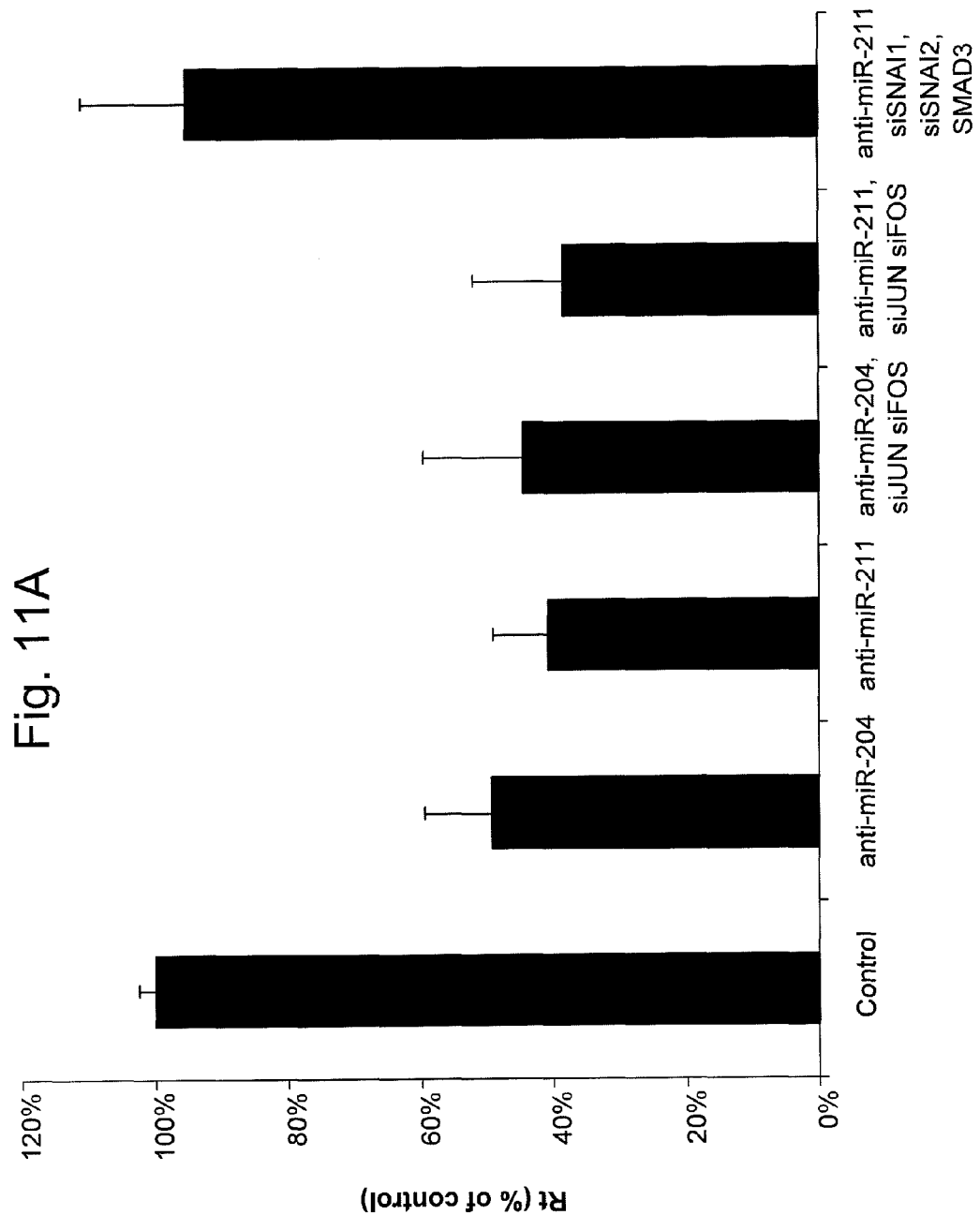

SEQUENCE LISTING

```
<160> NUMBER OF SEQ ID NOS: 7

<210> SEQ ID NO 1
<211> LENGTH: 22
<212> TYPE: RNA
<213> ORGANISM: Mus musculus

<400> SEQUENCE: 1
uucccuuugu cauccuaugc cu                                      22

<210> SEQ ID NO 2
<211> LENGTH: 23
<212> TYPE: RNA
<213> ORGANISM: Mus musculus

<400> SEQUENCE: 2
uucccuuugu cauccuaugc cug                                     23

<210> SEQ ID NO 3
<211> LENGTH: 22
<212> TYPE: RNA
<213> ORGANISM: Homo sapiens

<400> SEQUENCE: 3
uucccuuugu cauccuaugc cu                                      22

<210> SEQ ID NO 4
<211> LENGTH: 22
<212> TYPE: RNA
<213> ORGANISM: Mus musculus
```

```
<400> SEQUENCE: 4
uucccuuugu cauccuuugc cu                                          22

<210> SEQ ID NO 5
<211> LENGTH: 22
<212> TYPE: RNA
<213> ORGANISM: Homo sapiens

<400> SEQUENCE: 5
uucccuuugu cauccuucgc cu                                          22

<210> SEQ ID NO 6
<211> LENGTH: 21
<212> TYPE: RNA
<213> ORGANISM: Caenorhabditis elegans

<400> SEQUENCE: 6
uuguacuaca caaaaguacu g                                           21

<210> SEQ ID NO 7
<211> LENGTH: 68
<212> TYPE: DNA
<213> ORGANISM: Mus musculus

<400> SEQUENCE: 7
tggacttccc tttgtcatcc tatgcctgag aatatatgaa ggaggctggg aaggcaaagg  60
gacgttca                                                          68
```

MIR 204, MIR 211, THEIR ANTI-MIRS, AND THERAPEUTIC USES OF SAME

CROSS-REFERENCE TO RELATED APPLICATIONS

This patent application is a U.S. National Phase of International Patent Application No. PCT/US09/55000, filed Aug. 26, 2009, which claims the benefit of U.S. Provisional Patent Application. No. 61/092,102, filed Aug. 27, 2008, each of which are incorporated by reference.

INCORPORATION-BY-REFERENCE OF MATERIAL ELECTRONICALLY FILED

Incorporated by reference in its entirety herein is a computer-readable nucleotide/amino acid sequence listing submitted concurrently herewith and identified as follows: One 1,426 Byte ASCII (Text) file named "707349ST25.TXT," created on Dec. 22, 2010.

BACKGROUND OF THE INVENTION

Epithelial cells permit selective and regulated flux from apical to basolateral surfaces by transcellular or paracellular flux. Tight junctions form a continuous paracellular seal between apical and basolateral fluid compartments and control solute movement through the paracellular pathway across epithelia.

The retinal pigment epithelium (RPE) plays a role in regulating the microenvironment around the photoreceptors in the distal retina, where the events of phototransduction take place. Mutations of genes expressed in RPE have been associated with inherited retinal degenerative diseases, and damage to the RPE monolayer is thought to be an early event in age-related macular degeneration (AMD), the major cause of severe vision loss in people over the age of 60.

MicroRNAs (miRNAs or miRs) are a class of evolutionarily conserved noncoding RNAs encoded in the genomes of plants, invertebrates, and vertebrates. Many miRNAs are expressed in tissue-specific and developmental-stage-specific patterns, and changes in miRNA expression are observed in human pathologies.

There exists a need in the art for the identification and isolation of miRNAs and anti-miRNA molecules that interact with miRNAs and the use of these molecules to modulate miRNA-regulated biological functions, including those functions associated with epithelial tissues.

BRIEF SUMMARY OF THE INVENTION

An embodiment of the invention provides a method of preventing or treating detrimental epithelial cell proliferation or loss of epithelial cell differentiation in an individual comprising administering to an individual in need thereof an effective amount of miR 204, an effective amount of miR 211, or an effective amount of a mixture of miR 204 and miR 211.

Another embodiment of the invention provides a method of preventing or treating age-related macular degeneration or proliferative vitreal retinopathy in an individual comprising administering to an individual in need thereof an effective amount of miR 204 and/or miR 211.

A further embodiment of the invention provides a method of facilitating the transport of a substance across an epithelium in an individual comprising administrating to an individual an effective amount of anti-miR 204, an effective amount of anti-miR 211, or an effective amount of a mixture of anti-miR 204 and anti-miR 211.

An additional embodiment of the invention provides a pharmaceutical composition comprising substantially purified miR 204 and a pharmaceutically acceptable carrier. Another embodiment of the invention provides substantially purified miR 211 and a pharmaceutically acceptable carrier. A further embodiment of the invention provides a mixture of substantially purified miR 204 and miR 211 and a pharmaceutical carrier.

Another embodiment of the invention provides a pharmaceutical composition comprising substantially purified anti-miR 204 and a pharmaceutically acceptable carrier. Another embodiment of the invention provides substantially purified anti-miR 211 and a pharmaceutically acceptable carrier. A further embodiment of the invention provides a mixture of substantially purified anti-miR 204 and anti-miR 211 and a pharmaceutical carrier.

BRIEF DESCRIPTION OF THE DRAWINGS

FIG. 1A is a bar graph that shows six miRNAs enriched in human retinal pigment epithelium.

FIG. 1B is a bar graph that shows five miRNAs enriched in human neuroretina.

FIG. 2 is a bar graph that shows miRNA expression in cultured human fetal RPE (hfRPE)(n=3) compared to the average of miR expression levels in 20 tissues using the ΔΔCt method. P value is based on the t-test.

FIG. 9A is a bar graph that shows transepithelial electrical resistance (TER) decreased in cells transfected with a mixture of three anti-miRs.

FIG. 9B is a bar graph that shows TER deceased over time in anti-miR treated RPE. *, p<0.05, ** p<0.005.

FIG. 9D is a graph that shows TBH toxicity induced an increase in cell death and decrease in TER. Cells were treated with TBH for 4 hours (n=4) or 6 hours (n=5) or no serum free medium for 6 hours (control, n=5). Data for mean percent of cell death and mean percent decrease in TER (denoted by ■)

was connected with solid black line. Data for mean±SEM (denoted by ◆) was plotted in dotted lines. Data points within two doted lines or close to these lines are considered to have decrease in TER caused by cell death. Data from Anti-miR control (denoted by ▲) and anti-miR-222 (denoted by △) are close to the boundary denoted by dotted lines. Data from anti-miR-204 attached dead cells alone (denoted by ○) or anti-miR-204 counted with floating and attached dead cells (denoted by ●) are located away from the dotted lines.

Figure 10A:
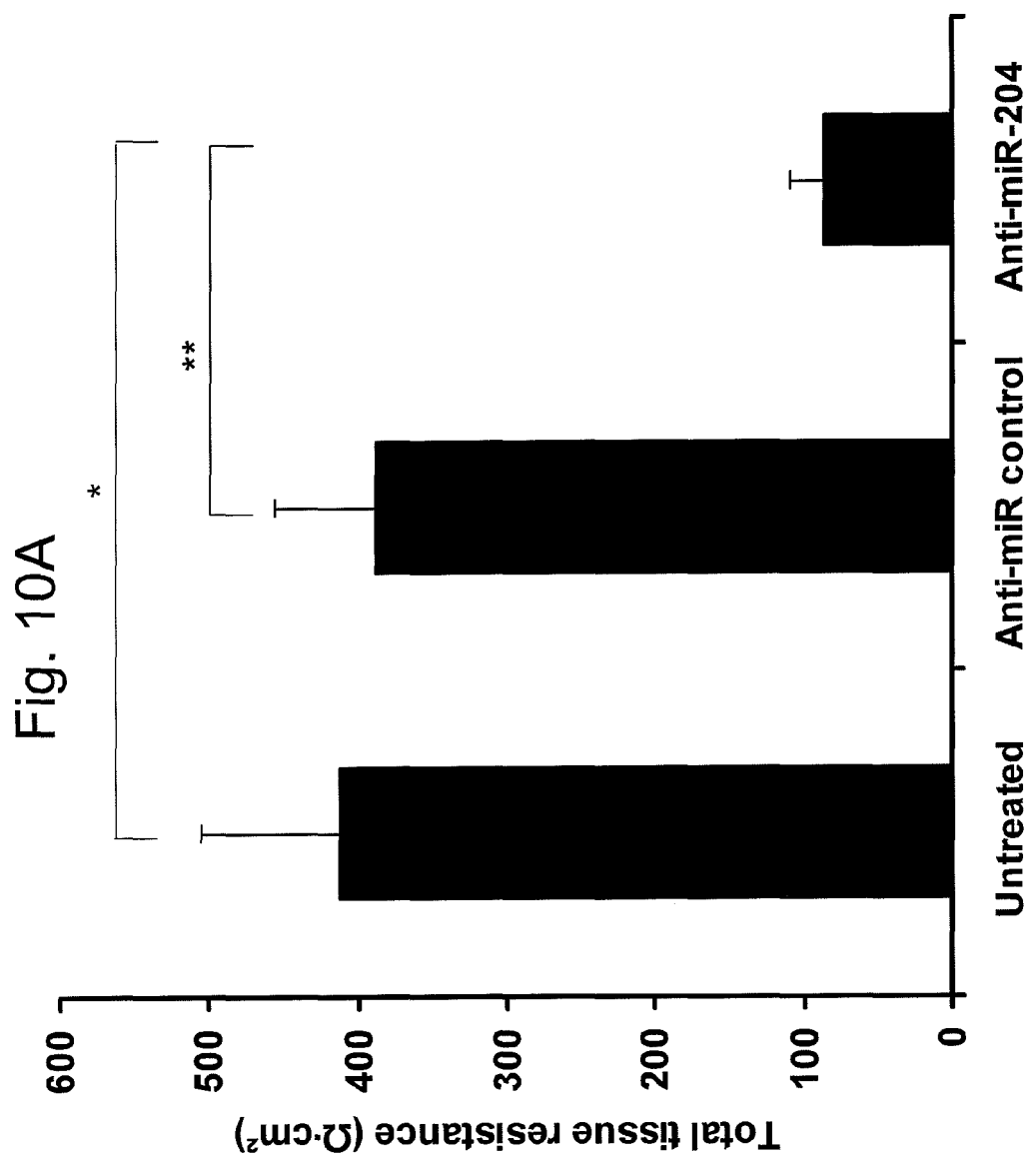

FIG. 10A is a bar graph that shows TER measured after mounting cells in a modified Üssing chamber. * $p<0.05$, ** $p<0.005$, Mean±SEM, n=7.

FIG. 10B is a bar graph that shows member potential measured with intracellular microelectrode recording. $V_A$, apical membrane potential; $V_B$, basolateral membrane potential. * $p<2\times10^{-10}$; ** $p<2\times10^{-13}$.

Figure 10C:
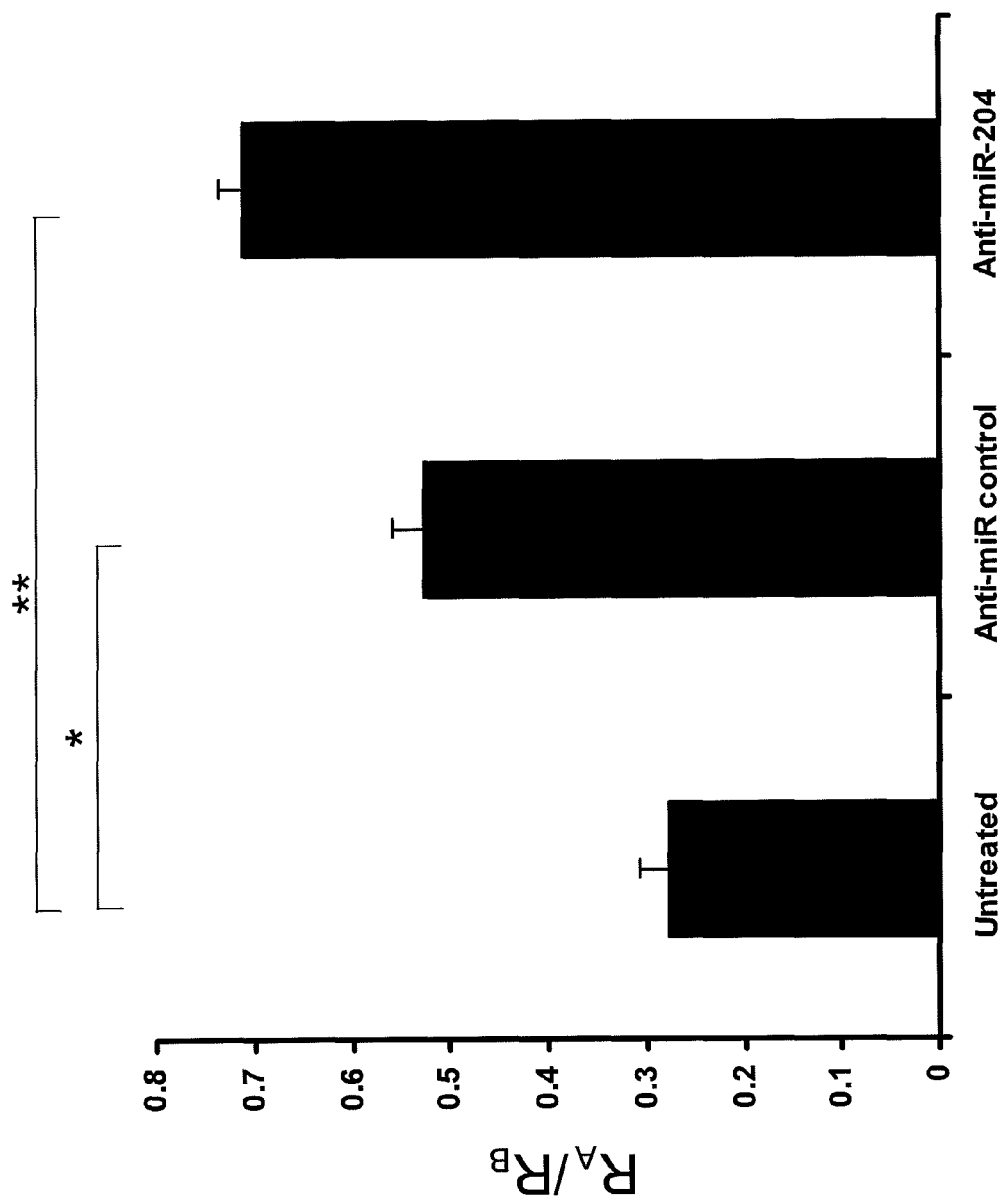

FIG. 10C is a bar graph that shows the ratio of the apical-to-basolateral membrane resistance of untreated, anti-miR control and anti-miR 204 treated cells. * $p<3\times10^{-5}$, ** $p<1\times10^{-13}$.

FIG. 11A is a bar graph that shows cells treated with anti-miR-204, anti-miR-211, anti-miR-204+ siRNA mixtures for JUN and FOS, anti-miR-211+ siRNA mixtures for JUN and FOS, anti-miR-211+ siRNA mixtures for SNAI1, SNAI2 and SMAD3.

Figure 11B:
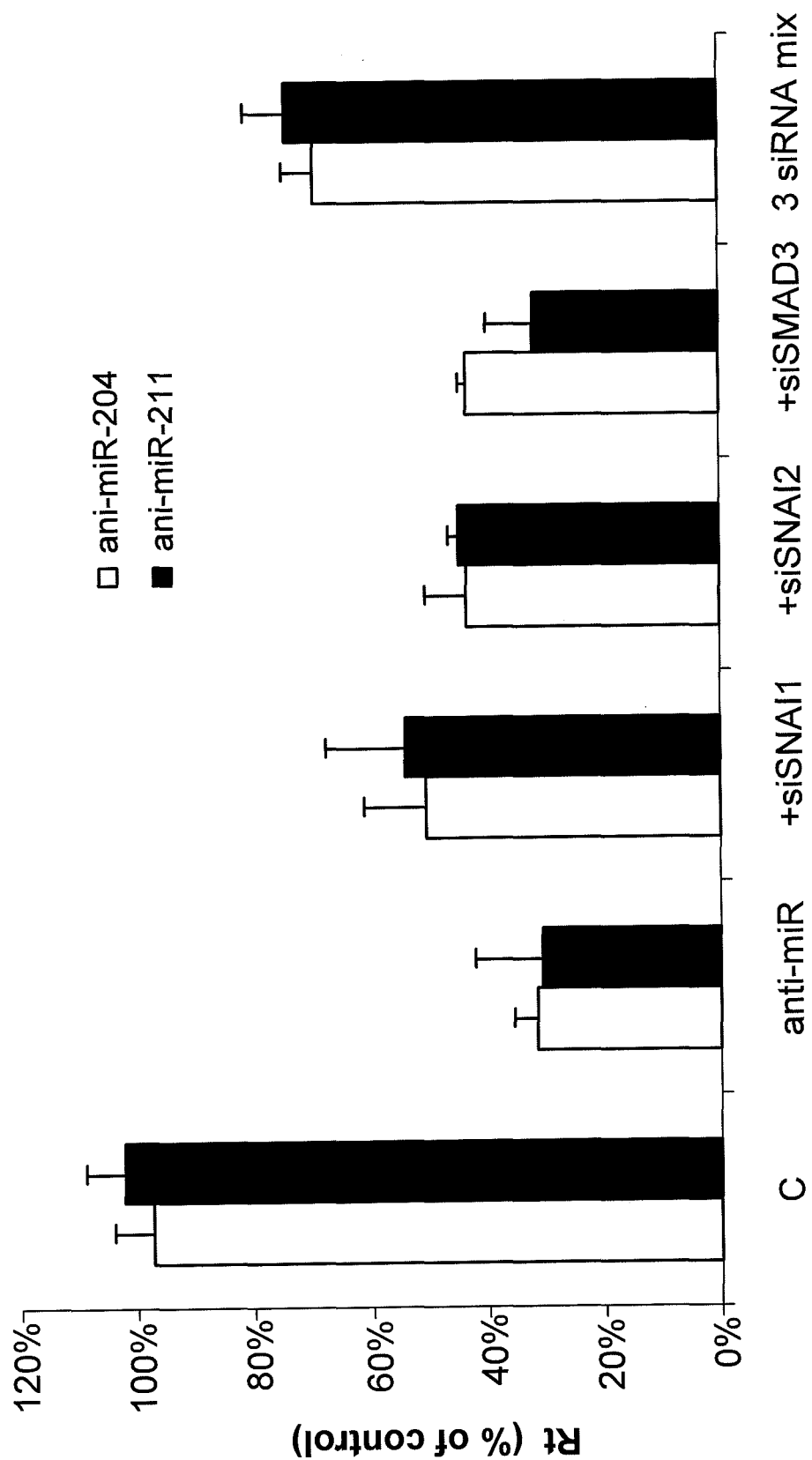

FIG. 11B is a bar graph that shows cells treated with anti-miR-204, anti-miR-211, anti-miR+ siRNA for SNAIL, anti-miR+ siRNA for SNAI2, anti-miR+ siRNA for SMAD3, anti-miR-211+ siRNA mixtures for SNAI1, SNAI2 and SMAD3.

Figure 12A:
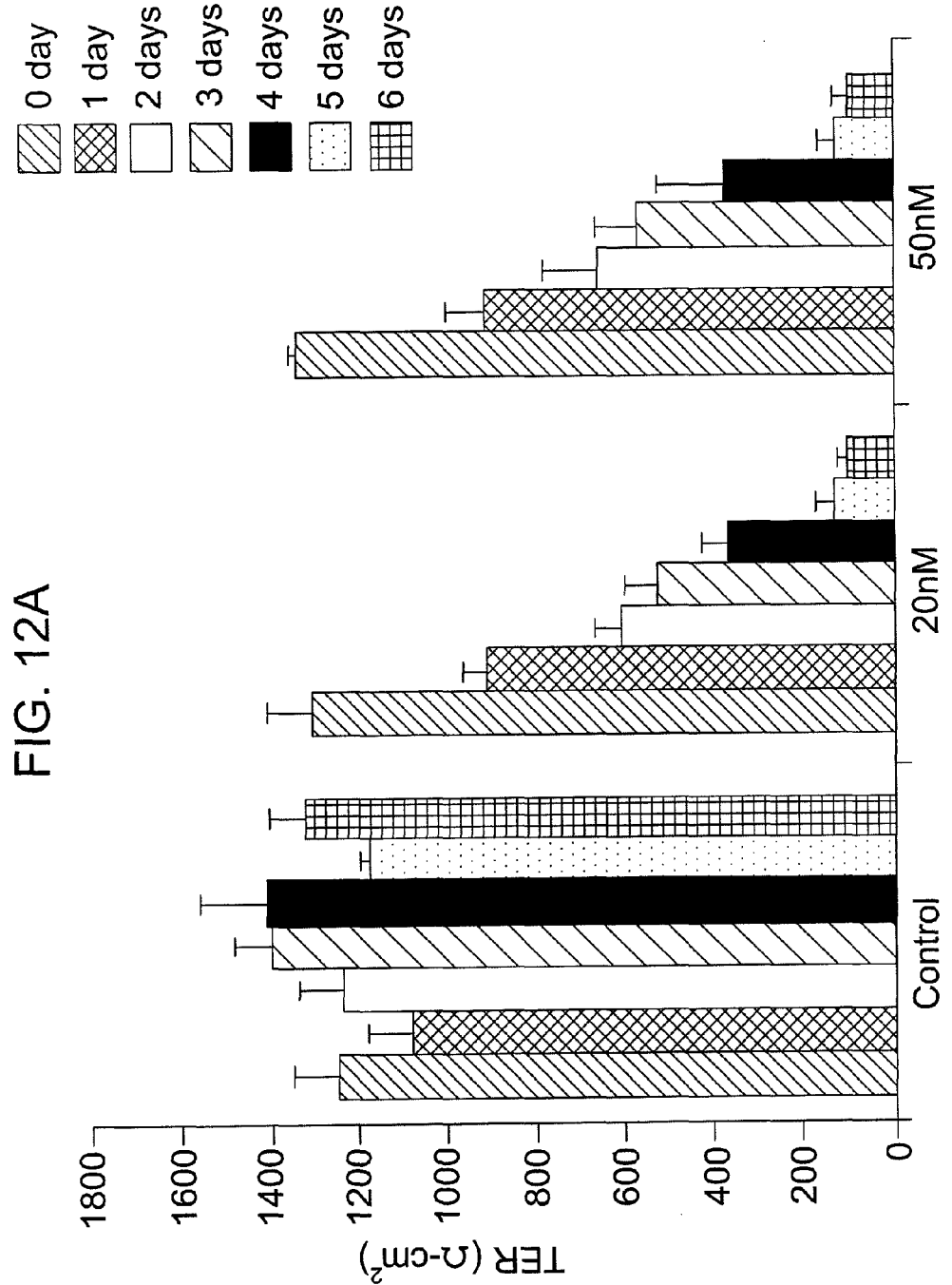

FIG. 12A is a bar graph that shows primary cultures of hfRPE transfected two times constitutively with Claudin-19 siRNA at 20 or 50 nM and TER recorded with EVOM over a total of 6 days.

Figure 12B:
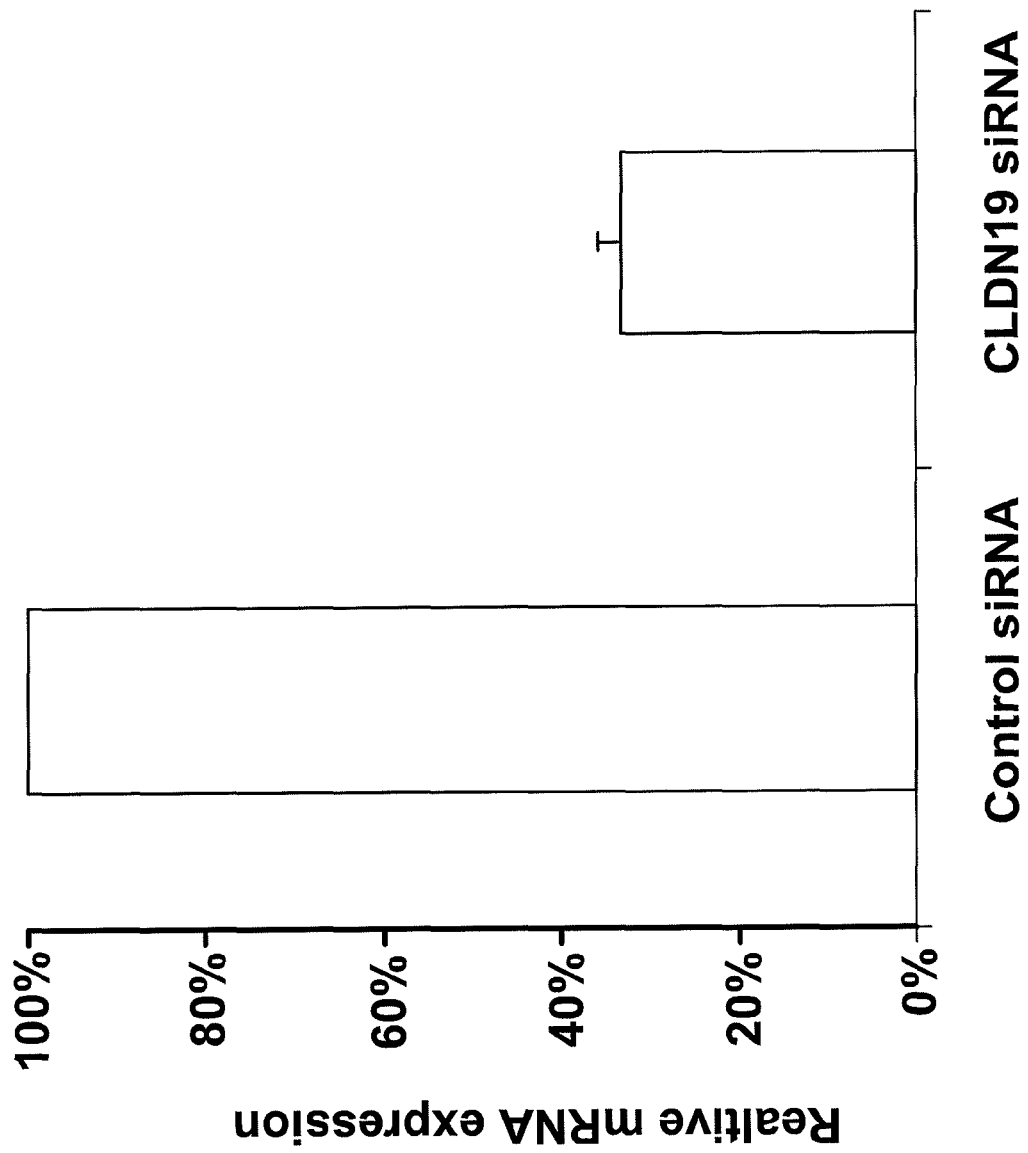

FIG. 12B is a bar graph that shows Claudin-19 mRNA assayed with Q PCR in cells transfected with Claudin-19 siRNA for 2 days.

Figure 13:
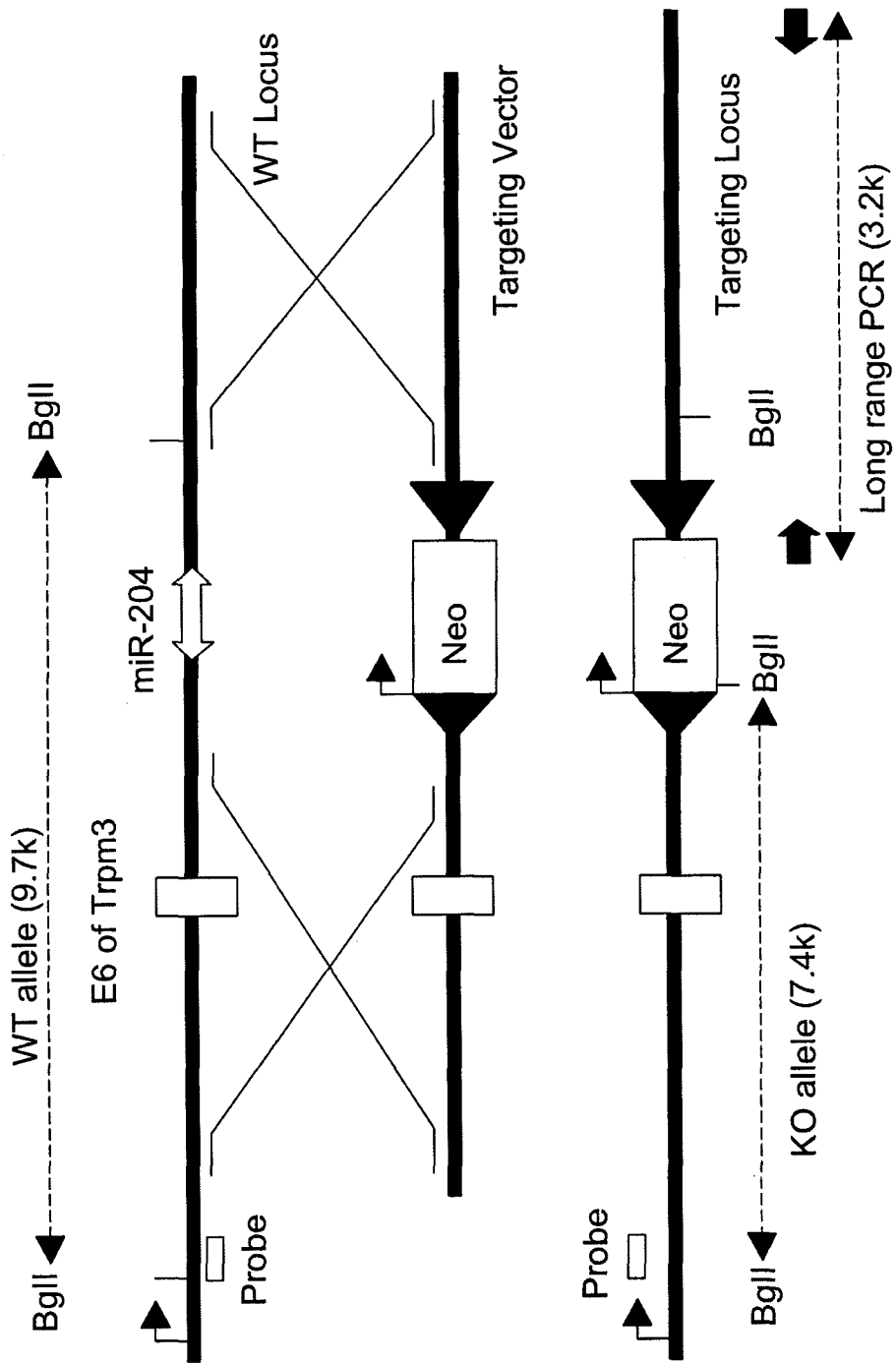

FIG. 13 diagrammatically shows a targeting strategy used for development of a miR-204 knockout (KO) mouse.

DETAILED DESCRIPTION OF THE INVENTION

An embodiment of the invention provides a method of preventing or treating detrimental epithelial cell proliferation or loss of epithelial cell differentiation in an individual comprising administering to an individual in need thereof an effective amount of miR 204 and/or miR 211.

Another embodiment of the invention provides a method of preventing or treating age-related macular degeneration or proliferative vitreal retinopathy in an individual comprising administering to an individual in need thereof an effective amount of miR 204 and/or miR 211, A further embodiment of the invention provides a method of facilitating the transport of a substance across an epithelium in an individual comprising administrating to an individual an effective amount of anti-miR 204 and/or anti-miR 211.

Additionally, another embodiment is the use of miR 204 or miR 211 or a mixture thereof in the manufacture of a medicament for the prevention or treatment of detrimental epithelial cell proliferation or loss of epithelial cell differentiation. Yet another embodiment is the use of miR 204 or miR 211 or a mixture thereof in the manufacture of a medicament for the prevention or treatment of age-related macular degeneration or proliferative vitreal retinopathy.

Preferably, the individual is a mammal. The mammal can be any suitable mammal, such as a mammal selected from the group consisting of a mouse, rat, guinea pig, hamster, cat, dog, pig, cow, horse, and primate. The mammal preferably is a human, especially a human patient.

The epithelium may be any type of simple epithelium, which is a single layer of epithelial cells, or stratified epithelium, which contains more than one layer of cells. The epithelial cell types may be squamous, cuboidal, or columnar. A mixed epithelium is a stratified epithelium in which more than one type of epithelial cell is present. Epithelial examples include RPE, the lens epithelium, the ciliary body, and epithelia of Schlemm's canal, which regulates the continuous removal of fluid from the eye. RPE is an example of a simple columnar epithelium.

Cell proliferation is an increase in the number of cells due to growth and division of those cells. Proliferative vitreal retinopathy (PVR) is a type of detrimental cell proliferation where additional epiretinal membranes form within the eye. Cell differentiation is the maturation of a cell into a more specialized type of cell. Detrimental loss of epithelial cell differentiation can be characterized by the loss of polarity, adhesion, and cohesion of differentiated epithelial cells. The epithelial-mesenchymal transition (EMT) is such a process, one in which the transitioned cells may become cancerous. Detrimental loss of differentiation is also present in PVR. Cancer is another form of detrimental cell proliferation wherein the cells often experience loss of differentiation.

Macular degeneration is the deterioration of the macula, a region of the eye within the retina, which provides high acuity vision. Macular degeneration is usually found in older adults and can severely impair vision. One form of macular degeneration is due to the atrophy of the RPE below the retina of the macula, which is often caused by the buildup of excess deposits of acellular debris.

Administration of anti-miR 204 and/or anti-miR 211 decreases the transepithelial electrical resistance (TER) of RPE. The TER is inversely related to the permeability of epithelial tissue. Therefore, administration of anti-miRNA directed against miR 204 and/or miR 211 in epithelium increases the permeability of the epithelium. Simple epithelial tissues comprise an apical surface (e.g., exposed to a lumen, such as the vitreous humour of the eye), a basal surface that attaches the epithelial tissue to other tissues, and lateral surfaces in which the cells of the epithelium tissue are attached to one another. The permeability of epithelial tissue is how "leaky" the epithelium is and is thus a measure of how permissively the tissue allows substances to be transported from the apical surface to the basal surface. Such transport across epithelial cells may occur via transcellular or paracellular flux. Transcellular flux is the transport of a substance through an epithelial cell, whereas paracellular transport is the transport of a substance within the space between epithelial cells. TER measures the paracellular flux of ions across epithelium. Without being bound to any theory, paracellular transport may be increased, for example, when contacts between adjacent epithelial cells are reduced, such as with the reduction of the number of tight junctions between the cells. Tight junctions are cell-cell contacts comprised of proteins associated with the cell membrane in which the proteins bind the cell membranes of the adjacent cells. Therefore, a decrease in the number of cell-cell tight junctions would allow for greater apical to basal flux of material.

Tight junctions are negatively regulated by several transcription factors, including WNK4, PKA, Snail, Slug, Smad3, Smad4, and Cingulin. Without being bound to any theory, anti-miR directed against the miRNA of any of these transcription factors could interact with the miRNA of these transcription factors, preventing the interaction of any messenger RNA of these transcription factors with the inhibitory miRNA. This would then increase the translation of these transcription factors and thus increase the presence of the transcription factors. This would in turn increase the negative regulation of tight junction proteins, thus decreasing the presence of tight junction proteins in the cell membranes of the epithelial cells.

Both proliferative vitreal retinopathy and macular degeneration involve uncontrollable RPE proliferation and loss of differentiation. These pathological outcomes may result from a disease-induced decrease in miR-204 levels in RPE. Reduction of miR-204 levels in human RPE causes loss of tight junction integrity and reduction of claudin 19 protein levels (as shown below in Example 1), which is normally highly expressed in human RPE and localized to the tight junctions. Eighty-five percent of all malignant cancers involve the loss of epithelial tight junctions. Administration of siRNA against claudin 19 (see below in Example 1) significantly reduced total epithelial resistance and increased the conductance of the paracellular or tight junction pathway. These data support the notion that miR-204-mediated conductance increases can initiate the proliferation of epithelia and blood vessel endothelia throughout the eye and in tumorgenic tissues throughout the body. Therefore, administration of miR 204 and/or miR 211 may be used to suppress proliferation and facilitate differentiation. Administration of mimics of miR 204 and/or miR 211 also may be used to suppress proliferation and facilitate differentiation.

Defects of miR-204 expression can also lead to other vision-impairing diseases such as diabetic retinopathy. For example, a decrease of miR-204 expression in retinal blood vessels could lead to loss of tight junction integrity and possible proliferation of vessels as observed in diabetic retinopathy. Thus, administration of miR-204 may be used to treat diabetic retinopathy.

Modulation of miR-204 levels may be used to treat glaucoma. For example, a decrease in miR-204 levels, such as through the administration of anti-miR-204, could open tight junctions of the cells that lie in Schlemm's canal and thereby increase the hydraulic conductivity of the outflow pathway to reduce the buildup of intraocular pressure, which is a main cause of glaucoma.

An increase in the permeability of an epithelium may allow for the increased transport of a substance across the epithelium or may allow for the transport of a substance across the epithelium, which may otherwise be excluded from transport. Such a substance may be a pharmaceutical. Administration of anti-miR 204 and/or anti-miR 211 may thus facilitate the transport of a pharmaceutical across an epithelium.

An additional embodiment of the invention provides a pharmaceutical composition comprising substantially purified miR 204 and a pharmaceutically acceptable carrier. Another embodiment of the invention provides substantially purified miR 211 and a pharmaceutically acceptable carrier. A further embodiment of the invention provides a mixture of substantially purified miR 204 and miR 211 and a pharmaceutical carrier.

Another embodiment of the invention provides a pharmaceutical composition comprising substantially purified anti-miR 204 and a pharmaceutically acceptable carrier. Another embodiment of the invention provides substantially purified anti-miR 211 and a pharmaceutically acceptable carrier. A further embodiment of the invention provides a mixture of substantially purified anti-miR 204 and anti-miR 211 and a pharmaceutical carrier.

There are two versions of the mature sequence of mouse miR204: 5'-UUCCCUUUGUCAUCCUAUGCCU-3' (SEQ ID NO: 1; miRBase Accession No. MIMAT0000237) and 5'-UUCCCUUUGUCAUCCUAUGCCUG-3' (SEQ ID NO: 2; GenBank Accession No. AJ560745). Based on the observation of a closely run doublet, both may exist in mice. The human mature miR204 has the sequence 5'-UUCCCUUUGUCAUCCUAUGCCU-3' (SEQ ID NO: 3; miRBase Accession No. MIMAT0000265). The sequence of mature mouse miRNA 211 is 5'-UUCCCUUUGUCAUCCUUUGCCU-3'; SEQ ID NO: 4 (miRBase Accession No. MIMAT0000668). The human mature miR211 has the sequence 5'-UUCCCUUUGUCAUCCUUCGCCU-3' (SEQ ID NO: 5; miRBase Accession No. MI0000287).

Most miRNAs imperfectly base-pair with the 3' untranslated region (UTR) of target mRNAs, and the 5' proximal "seed" region of miRNAs provide most of the pairing specificity. Without being bound to any theory, it is believed that the first eight miRNA nucleotides require greater specificity whereas the miRNA ribonucleotides 3' of this region allow for lower specificity and thus tolerate a higher degree of mismatched base pairing, with positions 2-7 being the most important. Anti-miRNAs to miRNA 204 and miRNA 211 may comprise, consist essentially of, and/or consist of nucleic acids that are complementary to the sequences of miRNA 204 and miRNA 211, respectively.

Mimics of miRNA 204, miRNA 211, anti-miR 204 and/or anti-miR 211 may be produced by many techniques known in the art. The 2' hydroxyl group of the ribose sugars may be alkylated, such as by methylation, to increase the stability of the molecule. Also, the ribose sugars may be modified by replacement of the hydroxyl group at the 2' position with a hydrogen, thus generating a DNA backbone. Also, any uracil base of an RNA sequence may be replaced by thymine. These are only a few non-limiting examples of the possible modifications that may be performed by a skilled artisan.

miRNA 204 and miRNA 211 have dramatically different expression patterns. Retinal pigment epithelial cells and melanocytes are the only two cell types that have high levels of miR-211 expression. Both cells also are the only two types in the body that can produce pigments and give color to eyes and skin, respectively. Without being bound by any theory, miR-211 may therefore be involved in the development of these two cell types. Also, miRNAs may effectuate different actions in different cell types. Therefore, miR-204 and/or miR-211 may work together with other miRs in a given cell type and the combinatorial effect would be different in each cell type.

The term "purified" does not require absolute purity or isolation; rather, it is intended as a relative term. Thus, for example, a purified (or isolated) protein preparation is one in which the protein is more pure than the protein in its natural environment within a cell. Such proteins may be produced, for example, by standard purification techniques, or by recombinant expression. In some embodiments, a preparation of a protein is purified such that the protein represents at least 50%, for example at least 70%, of the total protein content of the preparation.

An isolated biological component (such as a nucleic acid, peptide or protein) has been substantially separated, produced apart from, or purified away from other biological components in the cell of the organism in which the component naturally occurs, i.e., other chromosomal and extrachromosomal DNA and RNA, and proteins. Nucleic acids, peptides and proteins that have been isolated include nucleic acids and proteins purified by standard purification methods. The term also embraces nucleic acids, peptides, and proteins prepared by recombinant expression in a host cell as well as chemically synthesized nucleic acids.

A recombinant nucleic acid is one that has a sequence that is not naturally occurring or has a sequence that is made by an artificial combination of two otherwise separated segments of sequence. This artificial combination is often accomplished by chemical synthesis or, more commonly, by the artificial manipulation of isolated segments of nucleic acids, e.g., by genetic engineering techniques, such as those described in Sambrook et al. (In: Molecular Cloning: A Laboratory Manual, Cold Spring Harbor, N.Y., 1989).

By "nucleic acid" as used herein includes "polynucleotide," "oligonucleotide," and "nucleic acid molecule," and generally means a polymer of DNA or RNA, which can be single-stranded or double-stranded, synthesized or obtained (e.g., isolated and/or purified) from natural sources, which can contain natural, non-natural or altered nucleotides, and which can contain a natural, non-natural or altered internucleotide linkage, such as a phosphoroamidate linkage or a phosphorothioate linkage, instead of the phosphodiester found between the nucleotides of an unmodified oligonucleotide. It is generally preferred that the nucleic acid does not comprise any insertions, deletions, inversions, and/or substitutions. However, it may be suitable in some instances, as discussed herein, for the nucleic acid to comprise one or more insertions, deletions, inversions, and/or substitutions.

The nucleic acids of the invention may be recombinant. As used herein, the term "recombinant" refers to (i) molecules that are constructed outside living cells by joining natural or synthetic nucleic acid segments to nucleic acid molecules that can replicate in a living cell, or (ii) molecules that result from the replication of those described in (i) above. For purposes herein, the replication can be in vitro replication or in vivo replication.

The nucleic acids can be constructed based on chemical synthesis and/or enzymatic ligation reactions using procedures known in the art. See, for example, Sambrook et al., Molecular Cloning: A Laboratory Manual. 3rd ed., Cold Spring Harbor Press, Cold Spring Harbor, N.Y., 2001; and Ausubel et al., Current Protocols in Molecular Biology. Greene Publishing Associates and John Wiley & Sons, NY, 1994. For example, a nucleic acid can be chemically synthesized using naturally occurring nucleotides or variously modified nucleotides designed to increase the biological stability of the molecules or to increase the physical stability of the duplex formed upon hybridization (e.g., phosphorothioate derivatives and acridine-substituted nucleotides). Examples of modified nucleotides that can be used to generate the nucleic acids include, but are not limited to, 5-fluorouracil, 5-bromouracil, 5-chlorouracil, 5-iodouracil, hypoxanthine, xanthine, 4-acetylcytosine, 5-(carboxyhydroxymethyl)uracil, 5-carboxymethylaminomethyl-2-thiouridine, 5-carboxymethylaminomethyluracil, dihydrouracil, beta-D-galactosylqueosine, inosine, N6-isopentenyladenine, 1-methylguanine, 1-methylinosine, 2,2-dimethylguanine, 2-methyladenine, 2-methylguanine, 3-methylcytosine, 5-methylcytosine, N6-substituted adenine, 7-methylguanine, 5-methylaminomethyluracil, 5-methoxyaminomethyl-2-thiouracil, beta-D-mannosylqueosine, 5-methoxycarboxymethyluracil, 5-methoxyuracil, 2-methylthio-N6-isopentenyladenine, uracil-5-oxyacetic acid (v), wybutoxosine, pseudouracil, queosine, 2-thiocytosine, 5-methyl-2-thiouracil, 2-thiouracil, 4-thiouracil, 5-methyluracil, uracil-5-oxyacetic acid methylester, 3-(3-amino-3-N-2-carboxypropyl)uracil, and 2,6-diaminopurine. Alternatively, one or more of the nucleic acids of the invention can be purchased from companies, such as Macromolecular Resources (Fort Collins, Colo.) and Synthegen (Houston, Tex.).

The nucleic acid can comprise the nucleotide sequences of, e.g., SEQ ID NOS: 3 and/or 5. The nucleotide sequence alternatively can comprise a nucleotide sequence which is degenerate to, e.g., SEQ ID NOS: 3 and/or 5. The invention also provides an isolated or purified nucleic acid comprising a nucleotide sequence which is complementary to the nucleotide sequence of any of the nucleic acids described herein or a nucleotide sequence which hybridizes under stringent conditions to the nucleotide sequence of any of the nucleic acids described herein.

The nucleotide sequence which hybridizes under stringent conditions may hybridize under high stringency conditions. By "high stringency conditions" is meant that the nucleotide sequence specifically hybridizes to a target sequence (the nucleotide sequence of any of the nucleic acids described herein) in an amount that is detectably stronger than non-specific hybridization. High stringency conditions include conditions which would distinguish a polynucleotide with an exact complementary sequence, or one containing only a few scattered mismatches from a random sequence that happened to have a few small regions (e.g., 3-10 bases) that matched the nucleotide sequence. Such small regions of complementarity are more easily melted than a full-length complement of 14-17 or more bases, and high stringency hybridization makes them easily distinguishable. Relatively high stringency conditions would include, for example, low salt and/or high temperature conditions, such as provided by about 0.02-0.1 M NaCl or the equivalent, at temperatures of about 50-70° C. Such high stringency conditions tolerate little, if any, mismatch between the nucleotide sequence and the template or target strand. It is generally appreciated that conditions can be rendered more stringent by the addition of increasing amounts of formamide.

The nucleic acids of the invention can be incorporated into a recombinant expression vector. In this regard, the invention provides recombinant expression vectors comprising any of the nucleic acids of the invention. For purposes herein, the term "recombinant expression vector" means a genetically-modified oligonucleotide or polynucleotide construct that permits the expression of an RNA, protein, polypeptide, or peptide by a host cell, when the construct comprises a nucleotide sequence encoding the RNA, protein, polypeptide, or peptide, and the vector is contacted with the cell under conditions sufficient to have the RNA, protein, polypeptide, or peptide expressed within the cell. The vectors of the invention are not naturally-occurring as a whole. However, parts of the vectors can be naturally-occurring. The inventive recombinant expression vectors can comprise any type of nucleotides, including, but not limited to DNA and RNA, which can be single-stranded or double-stranded, synthesized or obtained in part from natural sources, and which can contain natural, non-natural or altered nucleotides. The recombinant expression vectors can comprise naturally-occurring, non-naturally-occurring internucleotide linkages, or both types of linkages. Preferably, the non-naturally occurring or altered nucleotides or internucleotide linkages do not hinder the transcription or replication of the vector.

The recombinant expression vector of the invention can be any suitable recombinant expression vector, and can be used to transform or transfect any suitable host. Suitable vectors include those designed for propagation and expansion or for expression or both, such as plasmids and viruses. The vector can be selected from the group consisting of the pUC series (Fermentas Life Sciences, Burlington, Ontario), the pBluescript series (Stratagene, LaJolla, Calif.), the pET series (Novagen, Madison, Wis.), the pGEX series (Pharmacia Biotech, Uppsala, Sweden), and the pEX series (Clontech, Palo Alto, Calif.). Bacteriophage vectors, such as λGTIO, λGTI 1, λZapII (Stratagene, La Jolla, Calif.), λEMBL4, and λNMI 149, also can be used. Examples of plant expression vectors include pBIO1, pBI101.2, ρBI101.3, pBI121 and pBIN19 (Clontech, Palo Alto, Calif.). Examples of animal expression vectors include pEUK-C1, pMAM and pMAMneo (Clontech, Palo Alto, Calif.). Preferably, the recombinant expression vector is a viral vector, e.g., a retroviral vector.

The recombinant expression vectors of the invention can be prepared using standard recombinant DNA techniques described in, for example, Sambrook et al., supra, and Ausubel et al., supra. Constructs of expression vectors, which are circular or linear, can be prepared to contain a replication system functional in a prokaryotic or eukaryotic host cell.

Replication systems can be derived, e.g., from ColE1, 2μ plasmid, λ, V40, bovine papilloma virus, and the like.

Desirably, the recombinant expression vector comprises regulatory sequences, such as transcription and translation initiation and termination codons, which are specific to the type of host (e.g., bacterium, fungus, plant, or animal) into which the vector is to be introduced, as appropriate and taking into consideration whether the vector is DNA- or RNA-based.

The recombinant expression vector can include one or more marker genes, which allow for selection of transformed or transfected hosts. Marker genes include biocide resistance, e.g., resistance to antibiotics, heavy metals, etc., complementation in an auxotrophic host to provide prototrophy, and the like. Suitable marker genes for the inventive expression vectors include, for instance, neomycin/G418 resistance genes, hygromycin resistance genes, histidinol resistance genes, tetracycline resistance genes, and ampicillin resistance genes.

The recombinant expression vector can comprise a native or normative promoter operably linked to the nucleotide sequence encoding the miR 204, miR 211, anti-miR 204, anti-miR 211, and/or mimics thereof (including functional portions and functional variants thereof), or to the nucleotide sequence which is complementary to or which hybridizes to the nucleotide sequence encoding the RNA. The selection of promoters, e.g., strong, weak, inducible, tissue-specific and developmental-specific, is within the ordinary skill of the artisan. Similarly, the combining of a nucleotide sequence with a promoter is also within the skill of the artisan. The promoter can be a non-viral promoter or a viral promoter, e.g., a cytomegalovirus (CMV) promoter, an SV40 promoter, an RSV promoter, and a promoter found in the long-terminal repeat of the murine stem cell virus.

The inventive recombinant expression vectors can be designed for either transient expression, for stable expression, or for both. Also, the recombinant expression vectors can be made for constitutive expression or for inducible expression. Further, the recombinant expression vectors can be made to include a suicide gene.

As used herein, the term "suicide gene" refers to a gene that causes the cell expressing the suicide gene to die. The suicide gene can be a gene that confers sensitivity to an agent, e.g., a drug, upon the cell in which the gene is expressed, and causes the cell to die when the cell is contacted with or exposed to the agent. Suicide genes are known in the art (see, for example, Suicide Gene Therapy: Methods and Reviews, Springer, Caroline J. (Cancer Research UK Centre for Cancer Therapeutics at the Institute of Cancer Research, Sutton, Surrey, UK), Humana Press, 2004) and include, for example, the Herpes Simplex Virus (HSV) thymidine kinase (TK) gene, cytosine daminase, purine nucleoside phosphorylase, and nitroreductase.

The invention further provides a host cell comprising any of the recombinant expression vectors described herein. As used herein, the term "host cell" refers to any type of cell that can contain the inventive recombinant expression vector. The host cell can be a eukaryotic cell, e.g., plant, animal, fungi, or algae, or can be a prokaryotic cell, e.g., bacteria or protozoa. The host cell can be a cultured cell or a primary cell, i.e., isolated directly from an organism, e.g., a human. The host cell can be an adherent cell or a suspended cell, i.e., a cell that grows in suspension. Suitable host cells are known in the art and include, for instance, DH5α E. coli cells, Chinese hamster ovarian cells, monkey VERO cells, COS cells, HEK293 cells, and the like. For purposes of amplifying or replicating the recombinant expression vector, the host cell is preferably a prokaryotic cell, e.g., a DH5α cell.

The terms "treat," and "prevent" as well as words stemming therefrom, as used herein, do not necessarily imply 100% or complete treatment or prevention. Rather, there are varying degrees of treatment or prevention of which one of ordinary skill in the art recognizes as having a potential benefit or therapeutic effect. In this respect, the inventive methods can provide any amount of any level of treatment or prevention of a condition associated with miR 204 and/or miR 211, e.g., proliferative vitreal retinopathy due to the reduction of miR 204 and/or miR211, in a mammal. Furthermore, the treatment or prevention provided by the inventive method can include treatment or prevention of one or more conditions or symptoms of the disease being treated or prevented. Also, for purposes herein, "prevention" can encompass delaying the onset of the disease, or a symptom or condition thereof.

An "effective amount" refers to a dose that is adequate to prevent or treat detrimental epithelial cell proliferation or loss of epithelial cell differentiation in an individual or to prevent or treat age-related macular degeneration or proliferative vitreal retinopathy in an individual. Amounts effective for a therapeutic or prophylactic use will depend on, for example, the stage and severity of the disease or disorder being treated, the age, weight, and general state of health of the patient, and the judgment of the prescribing physician. The size of the dose will also be determined by the compound selected, method of administration, timing and frequency of administration as well as the existence, nature, and extent of any adverse side-effects that might accompany the administration of a particular compound and the desired physiological effect. It will be appreciated by one of skill in the art that various diseases or disorders could require prolonged treatment involving multiple administrations, perhaps using miR 204, miR 211, anti-miR 204, anti-miR 211 and/or mimics thereof in each or various rounds of administration.

A miR, an anti-miR, and mimics thereof can be administered in a composition (e.g., pharmaceutical composition) that can comprise at least one carrier (e.g., a pharmaceutically acceptable carrier), as well as other therapeutic agents (e.g., other miRs, anti-miRs, and/or mimics thereof). The composition can be administered by any suitable route, including parenteral, topical, oral, or local administration.

The pharmaceutically acceptable carrier (or excipient) is preferably one that is chemically inert to the anti-miR, miR, and/or mimics thereof and one that has little or no side effects or toxicity under the conditions of use. Such pharmaceutically acceptable carriers include, but are not limited to, water, saline, Cremophor EL (Sigma Chemical Co., St. Louis, Mo.), propylene glycol, polyethylene glycol, alcohol, and combinations thereof. The choice of carrier will be determined in part by the particular anti-miR, miR, and/or mimics thereof as well as by the particular method used to administer the composition. Accordingly, there is a wide variety of suitable formulations of the composition.

The pharmaceutical composition in the context of an embodiment of the invention can be, for example, in the form of a pill, capsule, or tablet, each containing a predetermined amount of one or more of the active compounds and preferably coated for ease of swallowing, in the form of a powder or granules, or in the form of a solution or suspension. For oral administration, fine powders or granules may contain diluting, dispersing, and or surface active agents and may be present, for example, in water or in a syrup, in capsules or sachets in the dry state, or in a nonaqueous solution or suspension wherein suspending agents may be included, or in tablets wherein binders and lubricants may be included. Components such as sweeteners, flavoring agents, preservatives (e.g., antimicrobial preservatives), suspending agents, thickening agents, and/or emulsifying agents also may be present in the pharmaceutical composition. When administered in the form of a liquid solution or suspension, the formulation can contain one or more of the active compounds and purified water. Optional components in the liquid solution or suspension include suitable preservatives (e.g., antimicrobial preservatives), buffering agents, solvents, and mixtures thereof. A component of the formulation may serve more than one function.

Preservatives may be used. Suitable preservatives may include, for example, methylparaben, propylparaben, sodium benzoate, and benzalkonium chloride. A mixture of two or more preservatives optionally may be used. The preservative or mixtures thereof are typically present in an amount of about 0.0001% to about 2% by weight of the total composition.

Suitable buffering agents may include, for example, citric acid, sodium citrate, phosphoric acid, potassium phosphate, and various other acids and salts. A mixture of two or more buffering agents optionally may be used. The buffering agent or mixtures thereof are typically present in an amount of about 0.001% to about 4% by weight of the total composition.

The following formulations for oral, aerosol, parenteral (e.g., subcutaneous, intravenous, intraarterial, intramuscular, intradermal, interperitoneal, and intrathecal), and rectal administration are merely exemplary and are in no way limiting.

Formulations suitable for oral administration can consist of (a) liquid solutions, such as an effective amount of the compound dissolved in diluents, such as water, saline, or orange juice; (b) capsules, sachets, tablets, lozenges, and troches, each containing a predetermined amount of the active ingredient, as solids or granules; (c) powders; (d) suspensions in an appropriate liquid; and (e) suitable emulsions. Liquid formulations may include diluents, such as water and alcohols, for example, ethanol, benzyl alcohol, and the polyethylene alcohols, either with or without the addition of a pharmaceutically acceptable surfactant, suspending agent, or emulsifying agent. Capsule forms can be of the ordinary hard- or soft-shelled gelatin type containing, for example, surfactants, lubricants, and inert fillers, such as lactose, sucrose, calcium phosphate, and cornstarch. Tablet forms can include one or more of lactose, sucrose, mannitol, corn starch, potato starch, alginic acid, microcrystalline cellulose, acacia, gelatin, guar gum, colloidal silicon dioxide, croscarmellose sodium, talc, magnesium stearate, calcium stearate, zinc stearate, stearic acid, and other excipients, colorants, diluents, buffering agents, disintegrating agents, moistening agents, preservatives, flavoring agents, and pharmacologically compatible carriers. Lozenge forms can comprise the active ingredient in a flavor, usually sucrose and acacia or tragacanth, as well as pastilles comprising the active ingredient in an inert base, such as gelatin and glycerin, or sucrose and acacia, emulsions, gels, and the like containing, in addition to the active ingredient, such carriers as are known in the art.

The miRs, anti-miRs, and mimics thereof, alone or in combination with other suitable components, can be made into aerosol formulations to be administered via inhalation. These aerosol formulations can be placed into pressurized acceptable propellants, such as dichlorodifluoromethane, propane, nitrogen, and the like. They also may be formulated as pharmaceuticals for non-pressured preparations, such as in a nebulizer or an atomizer.

Formulations suitable for parenteral administration include aqueous and non-aqueous, isotonic sterile injection solutions, which can contain anti-oxidants, buffers, bacteriostats, and solutes that render the formulation isotonic with the blood of the intended recipient, and aqueous and non-aqueous sterile suspensions that can include suspending agents, solubilizers, thickening agents, stabilizers, and preservatives. The miR, anti-miR, and mimics thereof may be administered in a physiologically acceptable diluent in a pharmaceutical carrier, such as a sterile liquid or mixture of liquids, including water, saline, aqueous dextrose and related sugar solutions, an alcohol, such as ethanol, isopropanol, or hexadecyl alcohol, glycols, such as propylene glycol or polyethylene glycol, glycerol ketals, such as 2,2-dimethyl-1,3-dioxolane-4-methanol, ethers, such as poly(ethyleneglycol) 400, an oil, a fatty acid, a fatty acid ester or glyceride, or an acetylated fatty acid glyceride with or without the addition of a pharmaceutically acceptable surfactant, such as a soap or a detergent, suspending agent, such as pectin, carbomers, methylcellulose, hydroxypropylmethylcellulose, or carboxymethylcellulose, or emulsifying agents and other pharmaceutical adjuvants.

Oils, which can be used in parenteral formulations, include petroleum, animal, vegetable, or synthetic oils. Specific examples of oils include peanut, soybean, sesame, cottonseed, corn, olive, petrolatum, and mineral. Suitable fatty acids for use in parenteral formulations include oleic acid, stearic acid, and isostearic acid. Ethyl oleate and isopropyl myristate are examples of suitable fatty acid esters.

Suitable soaps for use in parenteral formulations may include fatty alkali metal, ammonium, and triethanolamine salts, and suitable detergents include (a) cationic detergents such as, for example, dimethyl dialkyl ammonium halides, and alkyl pyridinium halides, (b) anionic detergents such as, for example, alkyl, aryl, and olefin sulfonates, alkyl, olefin, ether, and monoglyceride sulfates, and sulfosuccinates, (c) nonionic detergents such as, for example, fatty amine oxides, fatty acid alkanolamides, and polyoxyethylene-polypropylene copolymers, (d) amphoteric detergents such as, for example, alkyl-beta-aminopropionates, and 2-alkyl-imidazoline quaternary ammonium salts, and (3) mixtures thereof.

Suitable preservatives and buffers can be used in such formulations. In order to minimize or eliminate irritation at the site of injection, such compositions may contain one or more nonionic surfactants having a hydrophile-lipophile balance (HLB) of from about 12 to about 17. The quantity of surfactant in such formulations ranges from about 5% to about 15% by weight. Suitable surfactants include polyethylene sorbitan fatty acid esters, such as sorbitan monooleate and the high molecular weight adducts of ethylene oxide with a hydrophobic base, formed by the condensation of propylene oxide with propylene glycol. The parenteral formulations can be presented in unit-dose or multi-dose sealed containers, such as ampoules and vials, and can be stored in a freeze-dried (lyophilized) condition requiring only the addition of the sterile liquid carrier, for example, water, for injections, immediately prior to use. Extemporaneous injection solutions and suspensions can be prepared from sterile powders, granules, and tablets.

The miRs, anti-miRs, and mimics thereof may be administered as an injectable formulation. The requirements for effective pharmaceutical carriers for injectable compositions are well known to those of ordinary skill in the art. See Pharmaceutics and Pharmacy Practice, J. B. Lippincott Co., Philadelphia, Pa., Banker and Chalmers, eds., pages 238-250 (1982), and ASHP Handbook on Injectable Drugs, Toissel, 4th ed., pages 622-630 (1986).

Topical formulations, including those that are useful for transdermal drug release, are well known to those of skill in the art and are suitable in the context of embodiments of the invention for application to skin.

The concentration of a compound of embodiments of the invention in the pharmaceutical formulations can vary, e.g., from less than about 1%, usually at or at least about 10%, to as much as 20% to 50% or more by weight, and can be selected primarily by fluid volumes, and viscosities, in accordance with the particular mode of administration selected.

Methods for preparing administrable (e.g., parenterally administrable) compositions are known or apparent to those skilled in the art and are described in more detail in, for example, Remington's Pharmaceutical Science (17th ed., Mack Publishing Company, Easton, Pa., 1985).

In addition to the aforedescribed pharmaceutical compositions, the miRs, anti-miRs, and mimics thereof can be formulated as inclusion complexes, such as cyclodextrin inclusion complexes, or liposomes. Liposomes can serve to target the miRs, anti-miRs, and mimics thereof to a particular tissue. Liposomes also can be used to increase the half-life of the miRs, anti-miRs, and mimics thereof. Many methods are available for preparing liposomes, as described in, for example, Szoka et al., Ann. Rev. Biophys. Bioeng., 9:467 (1980) and U.S. Pat. Nos. 4,235,871, 4,501,728, 4,837,028, and 5,019,369.

When miRs, anti-miRs, and mimics thereof are administered with one or more additional therapeutic agents, one or more additional therapeutic agents can be coadministered to the mammal. By "coadministering" is meant administering one or more additional therapeutic agents and the miR, anti-miR, and/or mimics thereof sufficiently close in time such that the miR, anti-miR, and/or mimics thereof can enhance the effect of one or more additional therapeutic agents. In this regard, the miR, anti-miR, and/or mimics thereof can be administered first and the one or more additional therapeutic agents can be administered second, or vice versa. Alternatively, the miR, anti-miR, and/or mimics thereof and the one or more additional therapeutic agents can be administered simultaneously.

The delivery systems useful in the context of embodiments of the invention may include time-released, delayed release, and sustained release delivery systems such that the delivery of the inventive composition occurs prior to, and with sufficient time to cause, sensitization of the site to be treated. The inventive composition can be used in conjunction with other therapeutic agents or therapies. Such systems can avoid repeated administrations of the inventive composition, thereby increasing convenience to the subject and the physician, and may be particularly suitable for certain composition embodiments of the invention.

Many types of release delivery systems are available and known to those of ordinary skill in the art. They include polymer base systems such as poly(lactide-glycolide), copolyoxalates, polycaprolactones, polyesteramides, polyorthoesters, polyhydroxybutyric acid, and polyanhydrides. Microcapsules of the foregoing polymers containing drugs are described in, for example, U.S. Pat. No. 5,075,109. Delivery systems also include non-polymer systems that are lipids including sterols such as cholesterol, cholesterol esters, and fatty acids or neutral fats such as mono-di-and tri-glycerides; hydrogel release systems; sylastic systems; peptide based systems; wax coatings; compressed tablets using conventional binders and excipients; partially fused implants; and the like. Specific examples include, but are not limited to: (a) erosional systems in which the active composition is contained in a form within a matrix such as those described in U.S. Pat. Nos. 4,452,775, 4,667,014, 4,748,034, and 5,239,660 and (b) diffusional systems in which an active component permeates at a controlled rate from a polymer such as described in U.S. Pat. Nos. 3,832,253 and 3,854,480. In addition, pump-based hardware delivery systems can be used, some of which are adapted for implantation.

A number of transfection techniques are generally known in the art (see, e.g., Graham et al., Virology, 52:456-467 (1973); Sambrook et al., supra; Davis et al., Basic Methods in Molecular Biology, Elsevier (1986); and Chu et al., Gene, 13:97 (1981). Transfection methods include calcium phosphate co precipitation (see, e.g., Graham et al., supra), direct micro injection into cultured cells (see, e.g., Capecchi, Cell, 22:479-488 (1980)), electroporation (see, e.g., Shigekawa et al., BioTechniques, 6:742-751 (1988)), liposome mediated gene transfer (see, e.g., Mannino et al., BioTechniques, 6:682-690 (1988)), lipid mediated transduction (see, e.g., Feigner et al., Proc. Natl. Acad. Sci. USA, 84:7413-7417 (1987)), and nucleic acid delivery using high velocity microprojectiles (see, e.g., Klein et al., Nature, 327:70-73 (1987)).

The following example further illustrates the invention but, of course, should not be construed as in any way limiting its scope.

EXAMPLE 1

This example demonstrates that miR-204 and miR-211 are important in normal eye physiology.

Methods

Human Tissues: Human fetal eyes (16-20 weeks of gestation (WG)) were obtained from Advanced Bioscience Resources, Inc (Alameda, Calif.). The research followed the tenets of the Declaration of Helsinki and was reviewed and approved by National Institutes of Health Institutional Review Board (IRB). Calu-3 cell line was a generous gift of Dr. Terry Machen (Berkeley, Calif.).

Primary culture of human fetal RPE: Cells were cultured as previously described (Maminishkis et. al., Invest. Ophthalmol. Vis. Sci., 47:3612-3624 (2006)). All reagents were purchased from Sigma (St. Louis, Mo.), unless otherwise indicated. Briefly, the eyecup was incubated in dispase (Invitrogen, Carlsbad, Calif.) at 37° C. for 30 min, following removal of the anterior chamber and the vitreous. RPE were peeled from the choroid, washed with RPE culture medium and seeded in a T25 Primaria tissue culture flask (BD Bioscience, Franklin Lakes, N.J.). After 3-5 weeks, the confluent cells were trypsinized and seeded onto clear 12-well transwells at $1\text{-}2\times10^5$ per well (Corning Costar, Lowell, Mass.). Cells were used in experiments after six to eight weeks on transwell. TER was measured with an EVOM (World Precision Instruments, Sarasota, Fla.).

RNA Extraction: Total RNA was isolated in two fractions (> and <200 nt) using mirVana miRNA isolation kit (Ambion, Austin, Tex.) according to the manufacture's protocol. Human fetal eyes at 16 (three pairs) or 20 (three pairs) weeks of gestation were dissected to obtain retina, RPE, and choroid. After retina was collected from posterior globe, the monolayer of RPE was gently peeled off and choroid was dissected from sclera. Samples were lysed in 600 µl lysis/binding solution, homogenized with plastic pestle, and triturated with a 26 gauge needle until all visible clumps were dispersed. Large RNA (>200 nt) or small RNA (<200 nt) was extracted following the instruction of this mirVana kit. RNA from cultured hfRPE and Calu-3 were extracted using the same protocol as above. Total RNA for the FirstChoice® Survey Panel of 20 normal adult human tissues, two matched pairs of tumor tissues and adjacent normal tissue (Kidney and Lung) and two tumor cell lines (MCF-7 and G-401) were purchased from Ambion. RNA for the survey panel were pooled from 3 donors for the following 20 tissues: Adipose, Bladder, Brain, Cervix, Colon, Esophagus, Heart, Kidney, Liver, Lung, Ovary, Placenta, Prostate, Skeletal Muscle, Small Intestine, Spleen, Testes, Thymus, Thyroid, Trachea.

Reverse Transcription and Q PCR for miRNA: Reverse transcription was performed for 157 miRNAs in the TaqMan® MicroRNA Assays Human Panel Early Access Kit using the High Capacity cDNA Archive Kit (P/N: 4365409 and 4322171, Applied Biosystems, Foster City, Calif.) (Chen et al., Nucl. Acids Res., 33, e179 (2005)). Two 96-well plates were run for each RNA sample to cover the entire panel.

Real-time PCR was performed according to the protocol in the MicroRNA Assays Human Panel Early Access Kit on a 7900HT Sequence Detection System (P/N: 4329002, Applied Biosystems, Foster City, Calif.). Each RT product from the 96-well plates were run in triplicate or quadruplicate in a 384-well plate at 95° C. for 10 min, followed by 40 cycles of 95° C. for 15 s and 60° C. for 1 min. The threshold cycle ($C_T$) is defined as the fractional cycle number at which the fluorescence passes the fixed threshold. The expression level of each miRNA relative to the average Ct of let-7a and miR16 was determined using the $2^{-\Delta\Delta CT}$ method (Chen et al., Nucl. Acids Res., 33, e179 (2005)). Expression for miRNA in normal tissue or tumor cell lines were normalized using miR-16 alone because let-7a varies more among different tissues. miRNA expression profile for the NCI60 panel of 59 tumor cell lines and some normal tissues was obtained as in previous publication (Gaur et al., Cancer Res., 67:2456-2468 (2007)).

Taqman real time PCR for miRNAs is very sensitive and uses much less material. It would be very difficult to collect enough RNA from human fetal eye for microarray based profiling of miRNA. Each cell has approximately 10 pg of total RNA. One nanogram of small RNA was used per RT reaction and 0.067 ng small RNA per PCR reaction, equivalent to 0.335 ng total RNA or 33 cells. Ct at 37 is approximately one copy per PCR reaction (Lao et al., Biochem. Biophys. Res. Commun., 343:85-89 (2006)). Ct at 18 for miR-204 is equivalent to 262,144 per PCR reaction if amplification is 100% efficient. Thus, the estimated copy number for highest miR (miR-204) is approximately 10,000 per cell.

Reverse Transcription and Q PCR for mRNA: Q RT-PCR was used to quantify the relative amount of mRNA for each gene in all samples. Total mRNA was extracted from the cultured human fetal RPE cells using mirVana kit followed by the RNeasy mini Cleanup Kit (Qiagen, Valencia, Calif.). One microgram of total RNA is mixed with 1 µM Oligo(dT)$_{12-18}$ (Invitrogen, Carlsbad, Calif.) in 14 µl volume, incubated at 65° C. for 5 minutes, and quickly chill on ice. The first strand buffer (1× final), 0.5 mM dNTP, 1 U/µl RNaseOUT, 2.5 mM DTT, and 0.02 U/µl Omniscript Reverse Transcriptase (Qiagen, Valencia, Calif.) were added to RNA-primer mix. Each 20 µl RT reaction was incubated at 37° C. 60 minutes and following by 93° C. for 5 minutes. Q-PCR for 55 genes, selected based on miRNA target prediction and known physiological pathways, were done using TaqMan® Assays (Applied Biosystems, Foster City, Calif.) on an ABI 7900HT Sequence Detection System. A 10 µl PCR reaction for every gene of each sample was performed in duplicates. The relative mRNA quantity of each gene is normalized against total RNA and GAPDH using the using the $2^{-\Delta\Delta CT}$ method (Livak and Schmittgen, Methods, 25:402-408 (2001)).

Data Analysis for Q PCR: For each sample, Ct was normalized for miRNAs to those of the references (average Ct of let-7a and miR-16) for the same sample using the equation (Livak and Schmittgen, Methods, 2001, 25, 402-408): $\Delta Ct = avg\ Ct_{sample} - avg\ Ct_{reference}$ and standard deviation: $SD_{\Delta Ct} = [(SDCt\ reference)^2 + (SDCt\ sample)^2]^{1/2}$ when comparing miRNA expression in a given tissue to other tissues. In comparing RPE to neuroretina and to choroid, retina or choroid tissue is designated as a calibrator, where $\Delta\Delta Ct = \Delta Ct_{sample} - \Delta Ct_{calibrator}$. The $SD_{\Delta\Delta Ct}$ will be the same as $SD_{\Delta Ct}$ because the calibrator is set as an arbitrary constant. The range of fold difference ($2^{-\Delta\Delta Ct}$) was calculated using average $\Delta\Delta Ct$ from three biological repeats by incorporating the standard deviation of $\Delta\Delta Ct$.

A miRNA is defined as "enriched" in retinal pigment epithelium if its expression level is significantly higher (at least ten fold) than that in retina and choroid at both 16 and 20 weeks of gestation (4 pairs of comparison). Statistical comparisons were made using the Microsoft Excel Student's t-test (two tailed distribution; two unpaired samples with unequal variances). For each pair of comparisons, p<0.05 is regarded as significant.

Anti-miRNA Transfection: Anti-miRNA oligonucleotides for miRNAs enriched in RPE were transfected into cultured RPE cells according to established guidelines (Vermeulen et al., RNA, 13:723-730 (2007); Gregory et al., Nat. Cell Biol., 10:501-502 (2008)). Confluent hfRPE cells cultured on 12-well transwell plate (5-6×10$^5$ cells/well) were used in transfection. For each transfection, 2 µl DharmaFECT #4 transfection reagent was mixed with 48 µl of OPTI-MEM (Invitrogen, Carlsbad, Calif.) in one tube, while 5 µl of anti-miRNA (20 µM stock and 200 nM final) was mixed with 20 µl of 1× siRNA buffer and 25 µl of OPTI-MEM in another tube. After incubating 5 minutes at room temperature, the two tubes were mixed for 20 minutes. Cells were washed once with transfection medium (the complete cell culture medium without antibiotics). After adding 400 µl of transfection medium to the anti-miR mixture, the combined 500 µl transfection mix were loaded onto apical chamber of transwell. Transepithelial electrical resistance was measured before transfection and at various times after transfection with EVOM. Transfection was repeated every four days if experiments lasted longer than four days.

Live/Dead Assay: Cells were imaged under 10× objective on Zeiss Axioplan 2 using the scanning mode to take 260 images and cover the entire transwell (12500 µm×12700 µm). Images for all experiments (n=12 for anti-miR and n=18 for TBH) were taken with same exposure time and had same image intensity settings. Dead cells on each image covering entire transwell were counted using NIH Image J software with ITCN pluggin. All images were counted with the same settings: 8 µm for minimum cell size and 0.8 for threshold.

ELISA: hfRPE on inserts were transfected in triplicates with anti-miR-204 or anti-miR-211 for 10 days. Conditioned media were collected at four days after transfection and assayed for cytokine levels using SearchLight technology (Pierce Biotechnology, Woburn, Mass.). This proteomic array technique uses multiplexed sandwich ELISAs for the quantitative measurement of up to 16 cytokines in a sample per assay. Each sample was assayed for expression of 32 cytokines. Transthyretin (Prealbumin) ELISA was done according to manufacture's instruction (AssayPro, St. Charles, Mo.).

Electrophysiology: Calomel electrodes in series with Ringer solutions and agar bridges were used to measure the transepithelial potential (TEP). An intracellular microelectrode, referenced to either the apical (A) or basal (B) bath, was used to measure the membrane potentials, $V_A$ and $V_B$, where $TEP=V_B-V_A$ as previously described (Maminishkis et al., Invest. Ophthalmol. Vis. Sci., 47:3612-3624 (2006)). Conventional microelectrodes were made from borosilicate glass tubing with a filament (Sutter Instrument Co., Novato, Calif.) and were back-filled with 150 mM KCl, and had resistances of 110 to 150 M.

The TER and the ratio of the apical-to-basolateral membrane resistance ($R_A/R_B$) were obtained by passing 2 to 4 μA current pulses (i) across the tissue and measuring the resultant changes in TEP, $V_A$, and $V_B$. TER is the resultant change in TEP divided by the current amplitude; the $R_A/R_B$ ratio is the absolute value of the change in $V_A$ ($\Delta V_A$) divided by the change in $V_B$ ($\Delta V_B$), where $R_A/R_B = i \Delta V_A / i \Delta V_B$.

Immunofluorescence: All procedures were carried out at room temperature. Cells were fixed for 30 minutes in 4% formaldehyde-PBS, washed three times with PBS, and permeabilized and blocked for 30 minutes with 0.1% Triton X-100, 2% BSA, 2% FBS, 2% goat serum in PBS. Primary antibodies were labeled using the Zenon kit (Invitrogen Corp., Carlsbad, Calif.) according to the manufacturer's instructions. After staining with antibodies, cells were counterstained with 4',6'-diamino-2-phenylindole (DAPI; Prolong Gold; Invitrogen, Carlsbad, Calif.), and mounted on glass slides with antifade reagent, and imaged with a microscope (Axioplan 2 with ApoTome using Axiovision 3.4 software; Carl Zeiss, Inc., Dublin, Calif.).

Results miRNA expression profile in RPE, neuroretina and choroid: RNA from cultured human fetal RPE (hfRPE) cells were assayed twice for the entire ABI Taqman panel of 157 miRNAs. It was found that 136 of 157 miRNAs were detected and 95% of detected miRNAs had less than two fold difference between the technical repeats ($\Delta\Delta Ct<1$). Assuming that the standard detection limit for Q RT-PCR is a two fold difference, these data indicate that the Q PCR assays for miRNAs are reproducible. The Q PCR assay is efficient with Ct for 65% detected miRNAs in less than 30 cycles using 0.1 ng small RNA for each PCR reaction.

Figure 1C:
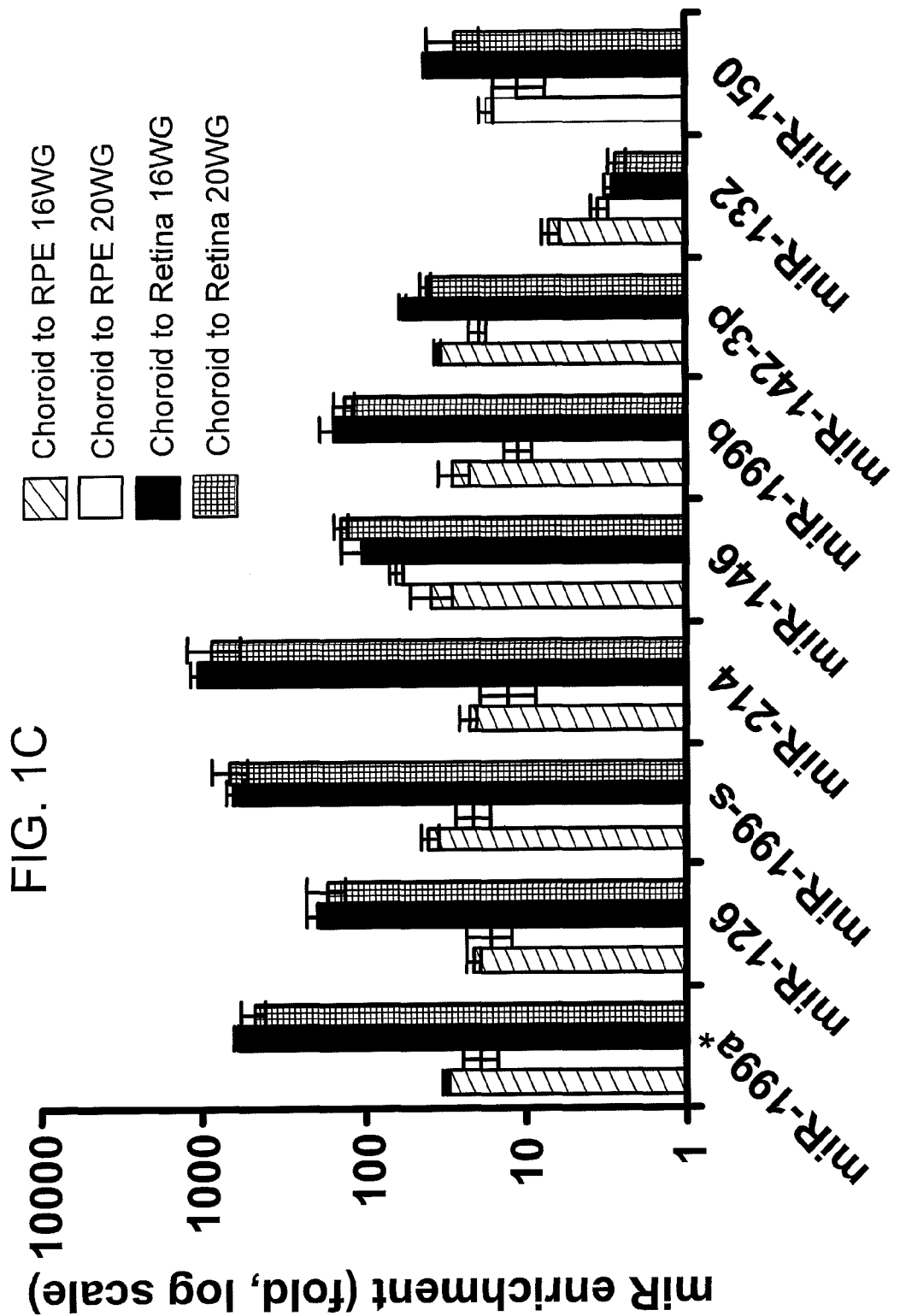
FIG. 1C is a bar graph that shows nine miRNAs enriched in human choroid.

RPE enriched miRNAs were obtained using the miRNA profiles from native hfRPE and the adjacent, retinal and choroidal tissues. FIGS. 1A, 1B, and 1C show the miR enrichment in RPE, retina, and choroid, respectively. (Fold difference was calculated using average $\Delta\Delta Ct$ from three biological repeats. A miRNA is considered as enriched in RPE if its expression level is significantly higher (at least 10 fold) than that in neuroretina and choroid at both 16 and 20 weeks of gestation. A two-tailed Student's test was run for each of the four pairs of comparison, p<0.05.) The expression profile for RPE, retina and choroid at 16 weeks were very similar to that of 20 weeks with only one miRNA that has more than 10 fold difference (p<0.05) between 16 and 20 WG in each of these three tissues. MiR-96 expression in choroid is 11 fold higher at 16 WG than at 20 WG (p<0.05). Expression levels for 31 miRNAs were 2 to 737 fold higher in RPE than in neuroretina and 43 miRNAs were 2 to 754 fold higher in RPE than in choroid. By definition, a miRNA is considered as "enriched" in RPE if its expression level is significantly (p<0.05, n=3) higher than that in neuroretina and choroid at both 16 and 20 weeks of gestation. There are 14 miRNAs with 10 to 400 fold higher expression in RPE than in neuroretina and 12 miRNAs with 10 to 500 fold higher expression in RPE than in choroid at 16WG (Table 1A).

TABLE 1A miRNAs enriched in RPE by comparing to retina and choroid at 16 WG.

16 WG

| RPE compared to Retina | | | | RPE compared to Choroid | | | |
|---|---|---|---|---|---|---|---|
| Name | (notes) | Fold | p Value | Name | (notes) | Fold | p Value |
| miR-184 | (1, 2) | 45 | 5E−03 | miR-184 | (1, 2) | 18 | 2E−02 |
| miR-187 | (1, 2) | 405 | 3E−03 | miR-187 | (1, 2) | 505 | 5E−03 |
| miR-200a | (1, 2) | 10 | 1E−02 | miR-200a | (1, 2) | 42 | 3E−02 |
| miR-204 | (1, 2) | 25 | 8E−04 | miR-204 | (1, 2) | 290 | 8E−04 |
| miR-211 | (1, 2) | 341 | 8E−03 | miR-211 | (1, 2) | 74 | 3E−03 |
| miR-222 | (1, 2) | 19 | 1E−02 | miR-222 | (1, 2) | 12 | 1E−02 |
| miR-302b | (1) | 10 | 3E−02 | miR-302b | (1) | 24 | 2E−02 |
| miR-302d | (1) | 26 | 1E−02 | miR-302d | (1) | 29 | 3E−03 |
| miR-125b | (3) | 10 | 1E−02 | miR-129 | (3) | 24 | 2E−03 |
| miR-126 | (3) | 10 | 4E−03 | miR-203 | (3) | 10 | 6E−03 |
| miR-199a* | (3) | 19 | 3E−03 | miR-9* | (3) | 19 | 2E−02 |
| miR-214 | (3) | 47 | 9E−03 | miR-9 | (3) | 17 | 4E−02 |
| miR-199-s | | 16 | 1E−03 | | | | |
| miR-221 | | 16 | 5E−02 | | | | |

Notes:
A (1) indicates miRNAs with higher expression in RPE than in retina and choroid at 16 WG or 20 WG.
A (2) indicates miRNAs more highly expressed in RPE than in retina and choroid at both 16 and 20 WG.
A (3) indicates miRNAs with a higher expression in RPE than in retina or choroid at both 16 WG and 20 WG.
See Table 1B for the corresponding 20 WG data.

At 20 WG, sixteen miRNAs were expressed at 10 to 737 fold higher in RPE than in neuroretina and 18 miRNAs with 10 to 754 fold higher expression in RPE than in choroid (Table 1B). There are eight and seven miRNAs enriched in RPE at 16WG and 20 WG, respectively. Six miRNAs (miR-184, 187, 200a, 204, 211, and 222) are enriched in RPE by a factor of 10 to 754 fold compared to neuroretina or choroid at both 16 and 20 WG. Two of the enriched miRNAs, miR-204 and miR-211, were also the mostly highly expressed miRNAs in RPE, ranging from 25 to 754 fold higher than in neuroretina and choroid.

TABLE 1B miRNAs enriched in RPE by comparing to retina and choroid at 20 WG.

20 WG

| RPE compared to Retina | | | | RPE compared to Choroid | | | |
|---|---|---|---|---|---|---|---|
| Name | (notes) | Fold | p Value | Name | (notes) | Fold | p Value |
| miR-184 | (1, 2) | 90 | 2E−02 | miR-184 | (1, 2) | 30 | 2E−03 |
| miR-187 | (1, 2) | 737 | 2E−03 | miR-187 | (1, 2) | 433 | 2E−04 |
| miR-200a | (1, 2) | 34 | 6E−05 | miR-200a | (1, 2) | 131 | 9E−05 |
| miR-204 | (1, 2) | 71 | 9E−03 | miR-204 | (1, 2) | 754 | 6E−03 |
| miR-211 | (1, 2) | 381 | 6E−03 | miR-211 | (1, 2) | 71 | 7E−05 |
| miR-222 | (1, 2) | 30 | 2E−03 | miR-222 | (1, 2) | 14 | 3E−03 |
| miR-200b | (1) | 31 | 4E−02 | miR-200b | (1) | 114 | 2E−04 |
| miR-125b | (3) | 12 | 3E−03 | miR-129 | (3) | 29 | 9E−03 |
| miR-126 | (3) | 10 | 2E−02 | miR-203 | (3) | 21 | 2E−03 |
| miR-199a* | (3) | 26 | 2E−02 | miR-9 | (3) | 171 | 2E−04 |
| miR-214 | (3) | 67 | 2E−02 | miR-9* | (3) | 98 | 7E−04 |
| miR-152 | | 19 | 7E−03 | miR-105 | | 28 | 3E−02 |
| miR-198 | | 11 | 3E−02 | miR-107 | | 14 | 8E−03 |
| miR-199b | | 12 | 3E−03 | miR-124a | | 10 | 2E−02 |
| miR-205 | | 102 | 3E−02 | miR-124b | | 16 | 6E−03 |
| miR-99a | | 10 | 3E−02 | miR-183 | | 10 | 3E−02 |
| | | | | miR-221 | | 12 | 7E−04 |
| | | | | miR-96 | | 17 | 5E−03 |

Notes:
A (1) indicates miRNAs with higher expression in RPE than in retina and choroid at 16 WG or 20 WG.
A (2) indicates miRNAs more highly expressed in RPE than in retina and choroid at both 16 and 20 WG.
A (3) indicates miRNAs with a higher expression in RPE than in retina or choroid at both 16 WG and 20 WG.
See Table 1A for the corresponding 16 WG data.

Eleven miRNAs were expressed at 12 to 55 fold higher in neuroretina than in RPE while the levels of 15 miRNAs were 12 to 855 fold higher in neuroretina than in choroid at 16 WG (Table 2A).

TABLE 2A miRNAs enriched in Retina by comparing to RPE and choroid at 16 WG.

16 WG

| Retina compared to RPE | | | | Retina compared to Choroid | | | |
|---|---|---|---|---|---|---|---|
| Name | (notes) | Fold | p Value | Name | (notes) | Fold | p Value |
| miR-124b | (1, 2) | 23 | 3E−02 | miR-124b | (1, 2) | 63 | 7E−03 |
| miR-135b | (1, 2) | 24 | 2E−02 | miR-135b | (1, 2) | 55 | 4E−03 |
| miR-182 | (1, 2) | 22 | 2E−02 | miR-182 | (1, 2) | 115 | 2E−02 |
| miR-183 | (1, 2) | 20 | 5E−02 | miR-183 | (1, 2) | 129 | 1E−02 |
| miR-96 | (1, 2) | 38 | 9E−03 | miR-96 | (1, 2) | 52 | 2E−02 |
| miR-149 | | 55 | 1E−02 | miR-149 | (1) | 125 | 6E−03 |
| miR-182* | | 22 | 1E−02 | miR-182* | (1) | 128 | 2E−02 |
| miR-216 | | 57 | 7E−04 | miR-216 | (1) | 202 | 3E−02 |
| miR-323 | | 12 | 2E−02 | miR-105 | (3) | 28 | 2E−03 |
| miR-368 | | 13 | 1E−02 | miR-124a | (3) | 135 | 2E−02 |
| miR-34b | | 14 | 4E−02 | miR-138 | (3) | 13 | 1E−02 |
| | | | | miR-204 | (3) | 12 | 8E−04 |
| | | | | miR-9 | (3) | 143 | 6E−03 |
| | | | | miR-9* | (3) | 88 | 2E−03 |
| | | | | miR-213 | | 11 | 2E−03 |

Notes:
A (1) indicates miRNAs with higher expression in retina than in RPE and choroid at 16 WG or 20 WG.
A (2) indicates miRNAs that are expressed higher in retina than in RPE and choroid at both 16 WG and 20 WG.
A (3) indicates miRNAs with higher expression in retina than in RPE or choroid at both 16 WG and 20 WG.
See Table 2B for the corresponding 20 WG data.

At 20 WG, neuroretina has 7 miRNAs expressed at 12 to 114 fold higher than RPE and 12 miRNAs expressed at 11 to 1148 fold higher than choroid (Table 2B). Eight miRNAs are enriched in neuroretina at 16 WG and six miRNAs are enriched at 20 WG.

TABLE 2B miRNAs enriched in Retina by comparing to RPE and Choroid at 20 WG.
20 WG

| Retina compared to RPE | | | | Retina compared to Choroid | | | |
|---|---|---|---|---|---|---|---|
| Name | (notes) | Fold | p Value | Name | (notes) | Fold | p Value |
| miR-124b | (1, 2) | 20 | 4E−03 | miR-124b | (1, 2) | 333 | 3E−03 |
| miR-135b | (1, 2) | 41 | 1E−04 | miR-135b | (1, 2) | 251 | 9E−04 |
| miR-182 | (1, 2) | 114 | 2E−02 | miR-182 | (1, 2) | 1148 | 2E−02 |
| miR-183 | (1, 2) | 32 | 4E−04 | miR-183 | (1, 2) | 308 | 5E−03 |
| miR-96 | (1, 2) | 50 | 3E−03 | miR-96 | (1, 2) | 832 | 3E−03 |
| miR-124a | (1) | 64 | 4E−03 | miR-124a | (1, 2, 3) | 634 | 1E−03 |
| miR-137 | | 12 | 1E−02 | miR-105 | (3) | 100 | 1E−02 |
| | | | | miR-138 | (3) | 11 | 4E−02 |
| | | | | miR-204 | (3) | 21 | 4E−02 |
| | | | | miR-9 | (3) | 577 | 2E−03 |
| | | | | miR-9* | (3) | 179 | 2E−03 |
| | | | | miR-95 | | 13 | 1E−02 |

Notes:
A (1) indicates miRNAs with higher expression in retina than in RPE and choroid at 16 WG or 20 WG.
A (2) indicates miRNAs that are expressed higher in retina than in RPE and choroid at both 16 WG and 20 WG.
A (3) indicates miRNAs with higher expression in retina than in RPE or choroid at both 16 WG and 20 WG.
See Table 2A for the corresponding 16 WG data.

Fifteen miRNAs were expressed at levels that are 12 to 40 fold higher in choroid than in RPE and while 18 miRNAs were 10 to 1042 fold higher in choroid than in neuroretina from eyes at 16 WG (Table 3A).

TABLE 3A miRNAs enriched in Choroid by comparing to RPE and Retina at 16 WG.
16 WG

| Choroid compared to RPE | | | | Choroid compared to Retina | | | |
|---|---|---|---|---|---|---|---|
| Name | (notes) | Fold | p Value | Name | (notes) | Fold | p Value |
| miR-126 | (1, 2) | 21 | 8E−04 | miR-126 | (1, 2) | 199 | 3E−05 |
| miR-142-3p | (1, 2) | 34 | 5E−02 | miR-142-3p | (1, 2) | 57 | 4E−03 |
| miR-146a | (1, 2) | 38 | 7E−03 | miR-146a | (1, 2) | 103 | 6E−03 |
| miR-150 | (1, 2) | 17 | 4E−02 | miR-150 | (1, 2) | 39 | 3E−05 |
| miR-199a* | (1, 2) | 31 | 1E−02 | miR-199a* | (1, 2) | 605 | 4E−06 |
| miR-199b | (1, 2) | 28 | 2E−03 | miR-199b | (1, 2) | 152 | 5E−04 |
| miR-199-s | (1, 2) | 40 | 1E−03 | miR-199-s | (1, 2) | 635 | 4E−06 |
| miR-214 | (1, 2) | 22 | 4E−02 | miR-214 | (1, 2) | 1042 | 6E−05 |
| miR-199a | (1, 2, 3) | 24 | 2E−03 | miR-199a | (1) | 10 | 1E−03 |
| miR-223 | (1) | 30 | 1E−02 | miR-223 | (1, 2, 3) | 37 | 3E−04 |
| miR-127 | (3) | 14 | 6E−03 | miR-23a | (3) | 16 | 2E−03 |
| miR-134 | (3) | 21 | 3E−03 | miR-99a | (3) | 43 | 3E−04 |
| miR-137 | (3) | 21 | 4E−02 | miR-100 | (3) | 42 | 2E−03 |
| miR-323 | (3) | 12 | 3E−02 | miR-125b | (3) | 11 | 8E−03 |
| miR-368 | (3) | 13 | 2E−02 | miR-139 | (3) | 10 | 5E−03 |
| | | | | miR-145 | (3) | 529 | 7E−04 |
| | | | | miR-152 | (3) | 13 | 3E−05 |
| | | | | miR-142-5p | | 17 | 1E−02 |

Notes:
A (1) indicates miRNAs with higher expression in choroid than in RPE and retina at 16 WG or 20 WG.
A (2) indicates miRNAs that are expressed higher in choroid than in RPE and retina at both 16 WG and 20 WG.
A (3) indicates miRNAs that have higher expression in choroid than in RPE or retina at both 16 WG and 20 WG.
See Table 3B for the corresponding 20 WG data.

In eyes at 20WG, choroid has 20 miRNAs expressed at 10 to 62 fold higher than RPE and 18 miRNAs expressed at 12 to 855 fold higher than neuroretina (Table 3B).

TABLE 3B miRNAs enriched in Choroid by comparing to RPE and Retina at 20 WG.
20 WG

| Choroid compared to RPE | | | | Choroid compared to Retina | | | |
|---|---|---|---|---|---|---|---|
| Name | (notes) | Fold | p Value | Name | (notes) | Fold | p Value |
| miR-126 | (1, 2) | 17 | 4E−03 | miR-126 | (1, 2) | 169 | 3E−03 |
| miR-142-3p | (1, 2) | 19 | 9E−03 | miR-142-3p | (1, 2) | 40 | 5E−04 |
| miR-146a | (1, 2) | 62 | 3E−03 | miR-146a | (1, 2) | 138 | 2E−04 |
| miR-150 | (1, 2) | 11 | 2E−02 | miR-150 | (1, 2) | 27 | 5E−03 |
| miR-199a* | (1, 2) | 19 | 2E−03 | miR-199a* | (1, 2) | 488 | 1E−02 |
| miR-199b | (1, 2) | 11 | 2E−03 | miR-199b | (1, 2) | 132 | 4E−04 |
| miR-199-s | (1, 2) | 21 | 9E−04 | miR-199-s | (1, 2) | 677 | 4E−02 |
| miR-214 | (1, 2) | 13 | 8E−03 | miR-214 | (1, 2) | 855 | 7E−03 |
| miR-139 | (1) | 13 | 6E−03 | miR-139 | (1, 2, 3) | 13 | 5E−03 |
| miR-145 | (1) | 11 | 2E−02 | miR-145 | (1, 2, 3) | 125 | 5E−02 |
| miR-155 | (1) | 21 | 2E−02 | miR-155 | (1) | 75 | 4E−02 |
| miR-127 | (3) | 12 | 2E−03 | miR-23a | (3) | 13 | 1E−02 |
| miR-134 | (3) | 17 | 9E−04 | miR-99a | (3) | 35 | 3E−02 |
| miR-137 | (3) | 13 | 7E−03 | miR-100 | (3) | 32 | 8E−04 |
| miR-199a | (3) | 12 | 7E−03 | miR-125b | (3) | 12 | 2E−03 |
| miR-323 | (3) | 10 | 3E−03 | miR-152 | (3) | 14 | 4E−03 |
| miR-368 | (3) | 17 | 5E−03 | miR-223 | (3) | 53 | 2E−02 |
| miR-154 | | 14 | 2E−02 | miR-10a | | 66 | 5E−02 |
| miR-154* | | 33 | 6E−03 | | | | |
| miR-299 | | 13 | 1E−02 | | | | |

Notes:
A (1) indicates miRNAs with higher expression in choroid than in RPE and retina at 16 WG or 20 WG.
A (2) indicates miRNAs that are expressed higher in choroid than in RPE and retina at both 16 WG and 20 WG.
A (3) indicates miRNAs that have higher expression in choroid than in RPE or retina at both 16 WG and 20 WG.
See Table 3A for the corresponding 16 WG data.

Based on this analysis, five miRNAs (miR-124b, 135b, 182, 183 and 96) and eight miRNAs (miR-126, 142-3p, 146a, 150, 199a*, 199b, 199-s, 214) were identified as enriched in neuroretina (see Tables 2A and 2B) and choroid (see Tables 3A and 3B), respectively. Expression levels of five miRNAs enriched in neuroretina were 20 to 1148 fold higher than that in RPE or choroid (see Tables 2A and 2B). Eight miRNAs were enriched in choroid by a factor of 10 to 1042 fold compared to neuroretina or RPE (see Tables 3A and 3B).

TABLE 4 miRNAs enriched in RPE, Retina and Choroid by combining 16 WG and 20 WG samples. Samples (n = 6) were pooled for each tissue between two age groups (16 and 20 WG, n = 3 each) before statistical analysis. Criteria for enrichment: p < 0.05 and >10 fold higher expression than the other two tissues.

| Name (notes) | Fold | p Value | Fold | p Value |
|---|---|---|---|---|
| | RPE compared to Choroid | | RPE compared to Retina | |
| miR-184 (1) | 11 | 3E−02 | 29 | 8E−03 |
| miR-187 (1) | 455 | 5E−08 | 488 | 7E−08 |
| miR-200a (1) | 79 | 3E−08 | 18 | 2E−05 |
| miR-204 (1) | 691 | 2E−06 | 42 | 3E−07 |
| miR-211 (1) | 75 | 1E−08 | 388 | 4E−06 |
| miR-222 (1) | 11 | 1E−05 | 23 | 2E−05 |
| miR-221 | 13 | 1E−05 | 17 | 3E−05 |
| miR-200b | 72 | 3E−06 | 16 | 6E−05 |

TABLE 4-continued miRNAs enriched in RPE, Retina and Choroid by combining 16 WG and 20 WG samples. Samples (n = 6) were pooled for each tissue between two age groups (16 and 20 WG, n = 3 each) before statistical analysis. Criteria for enrichment: p < 0.05 and >10 fold higher expression than the other two tissues.

| Name (notes) | Fold | p Value | Fold | p Value |
|---|---|---|---|---|
| | Retina compared to RPE | | Retina compared to Choroid | |
| miR-124a | 57 | 8E−05 | 302 | 1E−04 |
| miR-124b (1) | 22 | 9E−06 | 147 | 6E−05 |
| miR-135b (1) | 32 | 7E−05 | 115 | 2E−06 |
| miR-182 (1) | 57 | 2E−03 | 705 | 1E−03 |
| miR-183 (1) | 27 | 2E−05 | 199 | 4E−06 |
| miR-96 (1) | 42 | 1E−06 | 257 | 5E−04 |
| | Choroid compared to RPE | | Choroid compared to Retina | |
| miR-126 (1) | 18 | 5E−06 | 187 | 1E−09 |
| miR-139 | 21 | 3E−04 | 12 | 5E−06 |
| miR-142-3p(1) | 25 | 2E−05 | 48 | 2E−07 |
| miR-145 | 14 | 3E−04 | 258 | 3E−05 |
| miR-146a (1) | 48 | 1E−07 | 119 | 1E−07 |
| miR-150 (1) | 12 | 3E−05 | 35 | 1E−06 |
| miR-155 | 18 | 5E−04 | 53 | 3E−03 |
| miR-199a | 17 | 6E−06 | 21 | 4E−02 |
| miR-199a* (1) | 24 | 1E−06 | 538 | 4E−10 |
| miR-199b (1) | 17 | 4E−06 | 138 | 4E−09 |
| miR-199-s (1) | 28 | 8E−08 | 627 | 8E−08 |
| miR-214 (1) | 17 | 8E−06 | 909 | 4E−09 |

Notes:
A (1) indicates miRNAs that are the same as miRNAs identified by comparing 16 WG and 20 WG separately.

Since the miRNA expression profiles were very similar at 16 WG and 20 WG, data from both groups were combined for RPE, neuroretina and choroid before statistical analysis to see if more enriched miRs would be identified ($p<0.05$, >10 fold enrichment). Comparison from combined data identified all miRNAs enriched in RPE, neuroretina and choroid identified by comparing 16 WG and 20 WG separately. This method also identified two more RPE enriched miRNAs (miR-200b, -221), one more neuroretina enriched miRNA (miR-124a), and four more for choroid (miR-139, 145, 155, 199a) because of increased n for each group.

Figure 3:
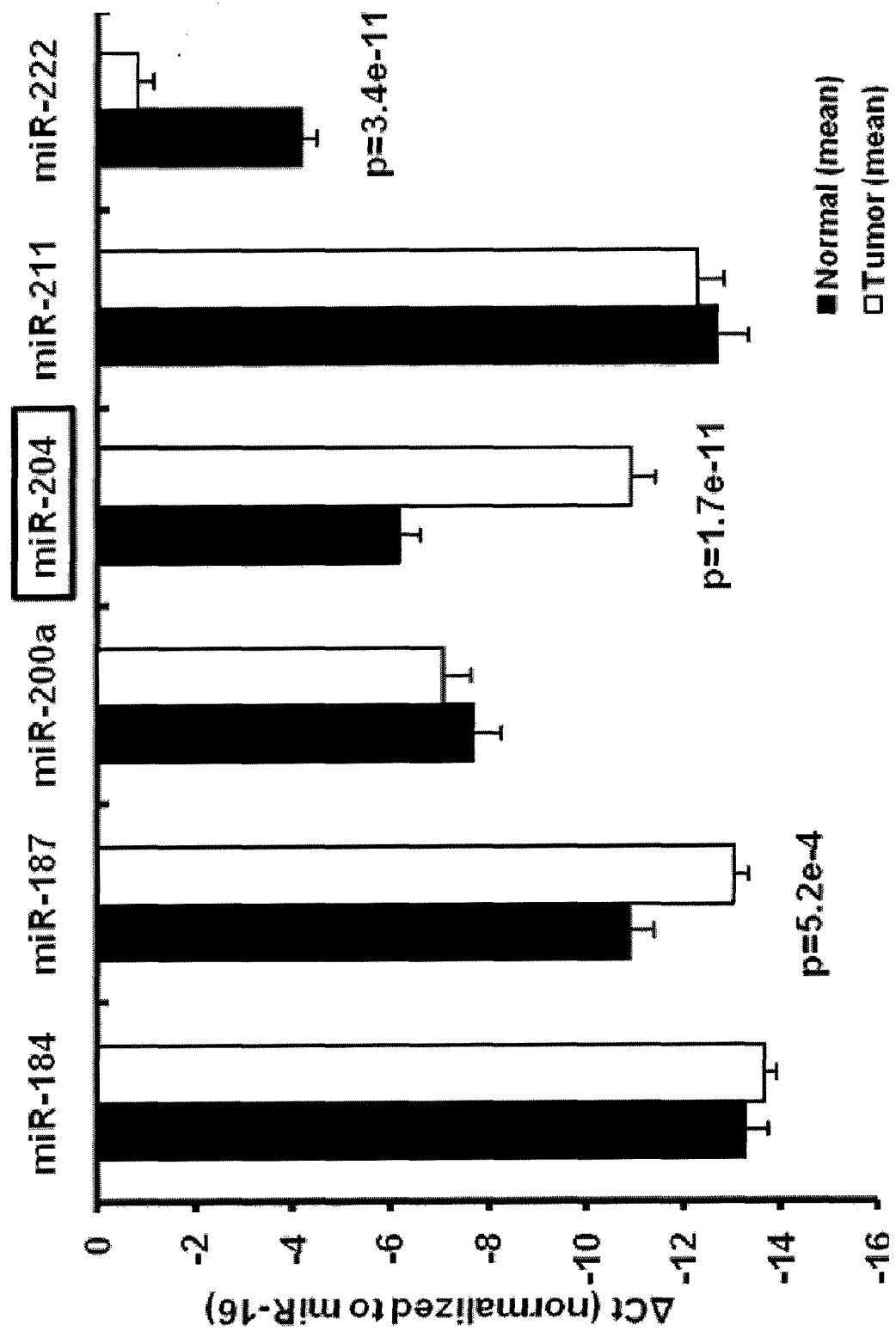
FIG. 3 is a bar graph that shows a comparison of miRNA expression in tumor compared to normal tissues. ΔCt (normalized to miR-16) is averaged from all tumor cell lines and tissues and compared to the average from all normal tissues (mean±STDEV).
Figure 4:
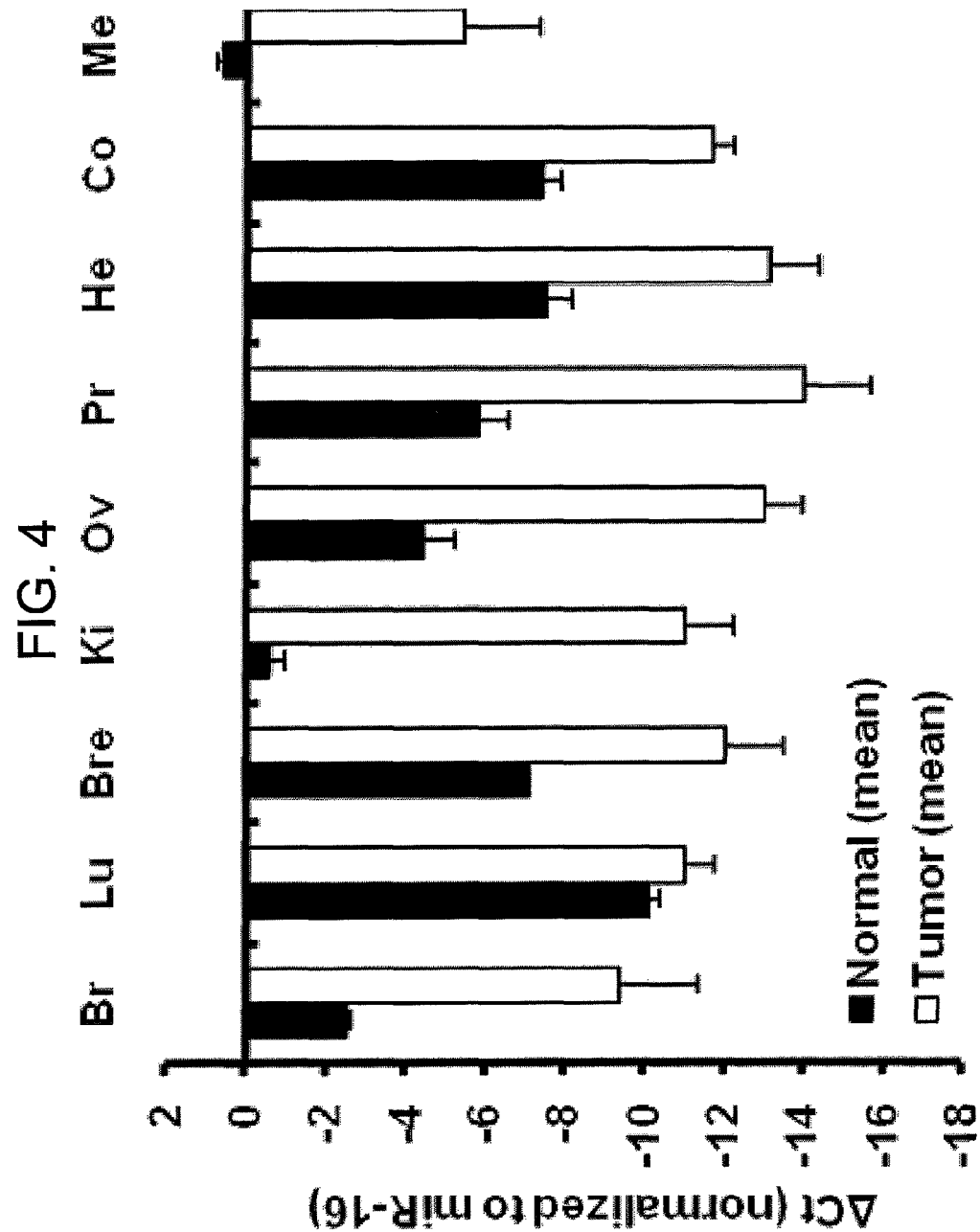
FIG. 4 is a bar graph that shows the expression of miR-204 in eight normal tissue types and miR-211 in normal melanocyte compared to their corresponding tumor cell lines. Br: brain; Lu: lung; Bre: breast; Ki: kidney; Ov: ovary; Pr: Prostate; He: hematological cells; Co: colon; Me: melanocyte. ΔCt is normalized to miR-16.

Expression of RPE enriched miRNAs in 20 other tissues: miR profiles were examined for the set of miRNAs enriched in RPE using 20 normal tissues. The expression level of let-7a is similar in RPE and among the 20 tissues and serves as a control for these comparisons. The results show that miRs 184 and 187 were expressed at much lower levels than the other three miRNAs across all 20 tissues. This observation suggests that these three enriched miRNA are relatively unique to human RPE. This conclusion was corroborated in three independent cultured hfRPE samples, which showed that miR-204, 211 and 222 are expressed at significantly higher levels relative to the 20 comparison tissues. FIG. 2 summarizes the relative expression levels for each of the six miRNAs in the three hfRPE cultures compared to the mean expression level in the 20 representative tissues ($\Delta\Delta Ct$ method). Five of the six miRNAs are significantly enriched in cultured RPE compared to the tissues from the rest of the body. Expression for miR-211 is more than $2.6\times10^4$ fold higher in RPE than the mean of 20 tissues ($p=7\times10^{-17}$) while miR-204 expression is 500 fold higher in RPE ($p=5\times10^{-10}$). Expression for miR-184, 187 and 222 are enriched in RPE by 112, 22 and 11 fold, respectively ($p<0.005$).

miR-204/211, 222 involvement in tumorigenesis: It has been extensively reported that expression for many miRNAs are significantly changed in tumors and play an important role in cell differentiation and tumorigenesis. The expression of the enriched set of miRNAs in tumor cells was profiled to see if any of these miRNAs changed significantly. The expression of the six RPE enriched miRNAs, as well as two tumor associated miRNAs, were profiled in 62 tumor cell lines, 2 tumor tissues and 29 normal tissues/primary cultures. FIG. 3 shows that the expression of miR-204 is approximately 30 fold lower in tumors compared to normal tissues ($p<2\times10^{-11}$) while expression for miR-146a, 155 and 187 are approximately three ($p<0.01$), five ($p<2\times10^{-4}$) and six ($p<6\times10^{-4}$) fold lower, respectively. The expression level for miR-222 is 10 fold higher in tumor vs. normal ($p<5\times10^{-11}$), indicating that it is a possible oncogenic marker. FIG. 4 shows miR-204 expression is significantly ($p<0.05$) lower in tumor than normal tissue in five of the nine groups (brain, kidney, ovary, hematological cells, and colon). miR-204 expression is also much lower in breast and prostate tumor tissue than in normal tissues but it is not statistically significant because of small sample size for normal tissues. miR-211 expression is much higher in primary culture of human melanocyte and possibly has a more dominant function than miR-204. Expression for miR-204 is not significantly different between melanocyte and melanoma but miR-211 is significantly lower in melanoma than in melanocyte. In summary, miR-204 or miR-211 expression is 20 to 1361 fold lower in eight of nine groups of tumor cells than in corresponding normal tissue.

Figure 5:
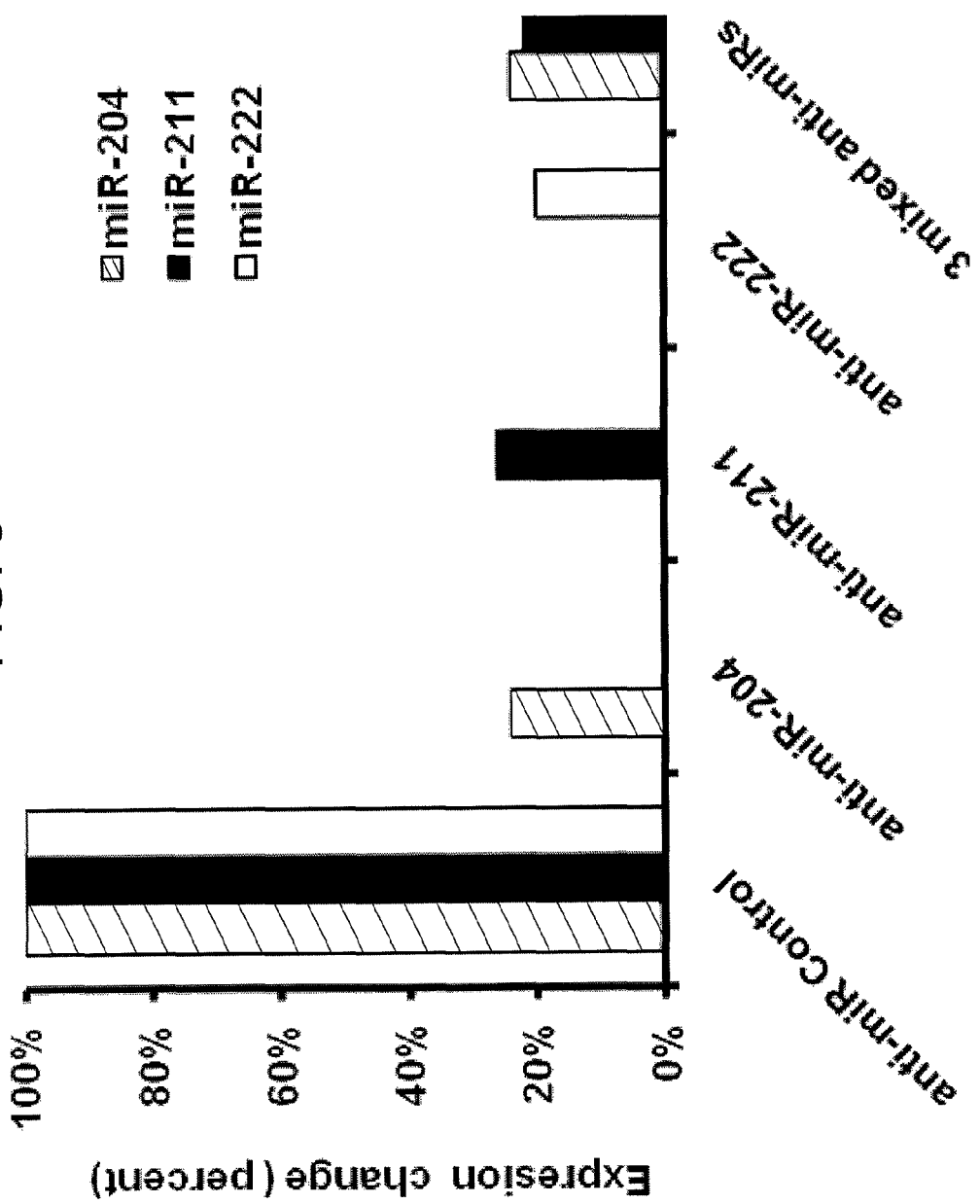
FIG. 5 is a bar graph that shows the level of miR expression assayed with Q PCR in hfRPE cells after anti-miR transfection for 48 hours. Cells were transfected with anti-miR control, anti-miR-204, anti-miR-211, anti-miR-222, or mix of anti-miR-204/211/222.

Gene expression specifically altered by anti-miR-204/211: To better understand how miR regulate gene expression in primary cultures of epithelial cells, changes in gene expression after transfecting cells with anti-miR or miR mimics were examined. First, transfection efficiency using a transfection indicator labeled with green fluorescence was examined. Cells regain hexagonal shape after 4 weeks in culture. The cells used were uniformly transfected throughout the transwell. Approximately 75% cells were transfected after a single transfection while triple transfections (every three days) significantly improved the rate to 75%. A series of experiments were initiated by using Q-PCR to determine if the relative levels of miRNA can be affected by transfection with specific miRNA mimics or anti-miRNAs. Since miRNA 204/211 are already very high in RPE, transfection did not increase miRNA level. Mature miRNA level decreased by 80% for miR-204, 211 or 222, using Q PCR assay after RPE was transfected with anti-miR-204, 211, 222, or mix of three anti-miRs (FIG. 5).

Figure 6:
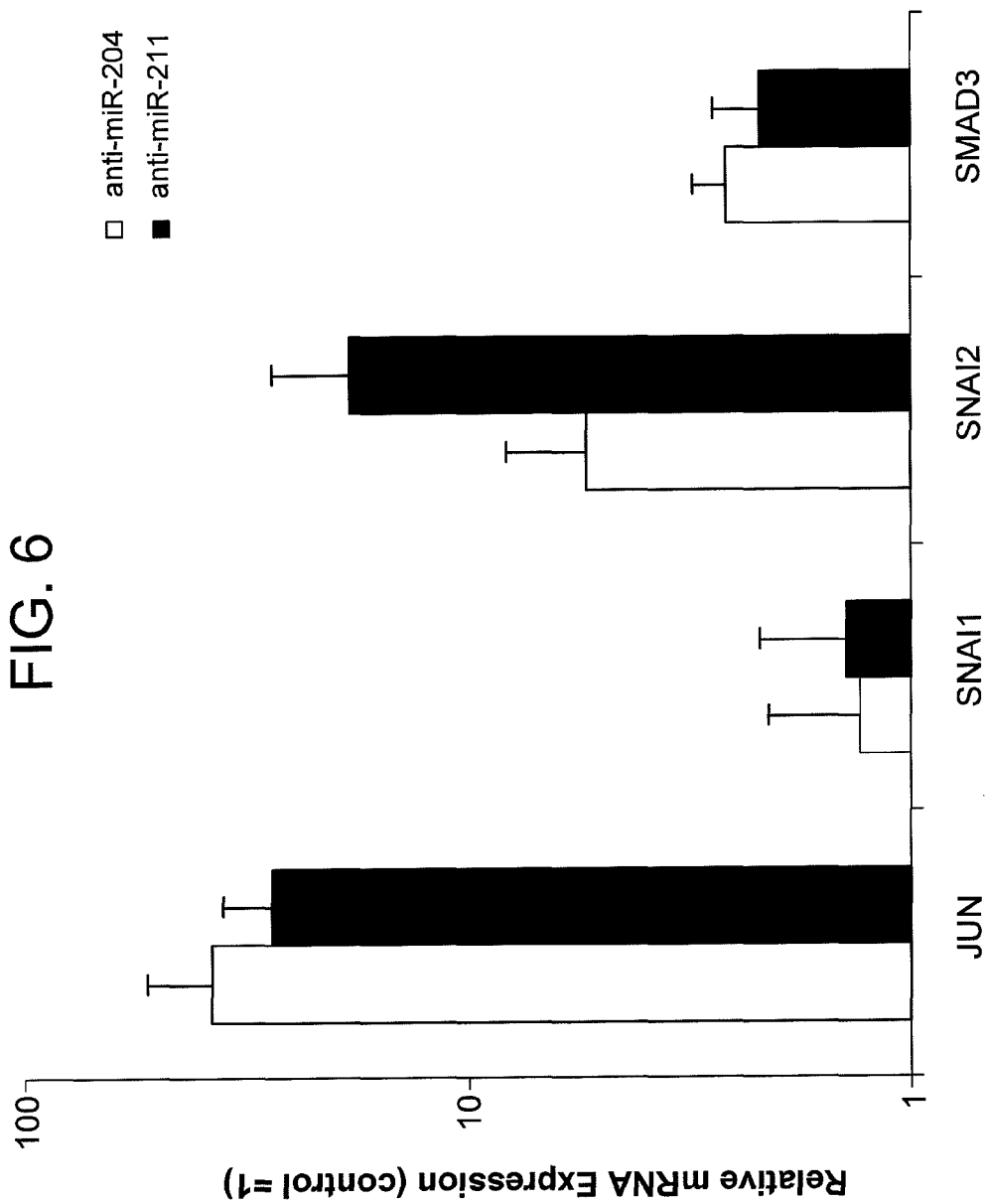
FIG. 6 is a bar graph that shows gene expression up-regulated in anti-miR treated RPE.

It has been shown that Jun/Fos, SNAI1 (Snail), SNAI2 (Slug), Smad3, Smad4, and Cingulin are transcriptions factors capable of regulating junctional protein expression in various cell types. FIG. 6 shows that the expression of many of these transcription factors is significantly increased following treatment with anti-miR-204 or 211. Transcription factors JUN/FOS, SNAI1, SNAI2 and SMAD3 are significantly upregulated in anti-miR-204 or anti-miR-211 treated cells. SNAI1 expression significantly increased by 2-3 fold ($n=4$, $p<0.05$), and SNAI2 expression was increased by 5-20 fold ($n=4$, $p<0.05$), and SMAD3 expression was upregulated 2-4 fold ($n=4$, $p<0.001$) in anti-miR-204 or anti-miR-211 experiments. JUN expression was increased more dramatically (30-50 fold, $n=4$, $p<0.001$). Anti-miR-204/211 significantly upregulated expression levels for PDGFA, PDGFRB, ROCK1, ROCK2, and RHOB ($n=4$, $p<0.001$), genes that regulate cell growth (PDGF family) and disruption of tight junction (ROCK1, 2, RHOB).

Figure 7:
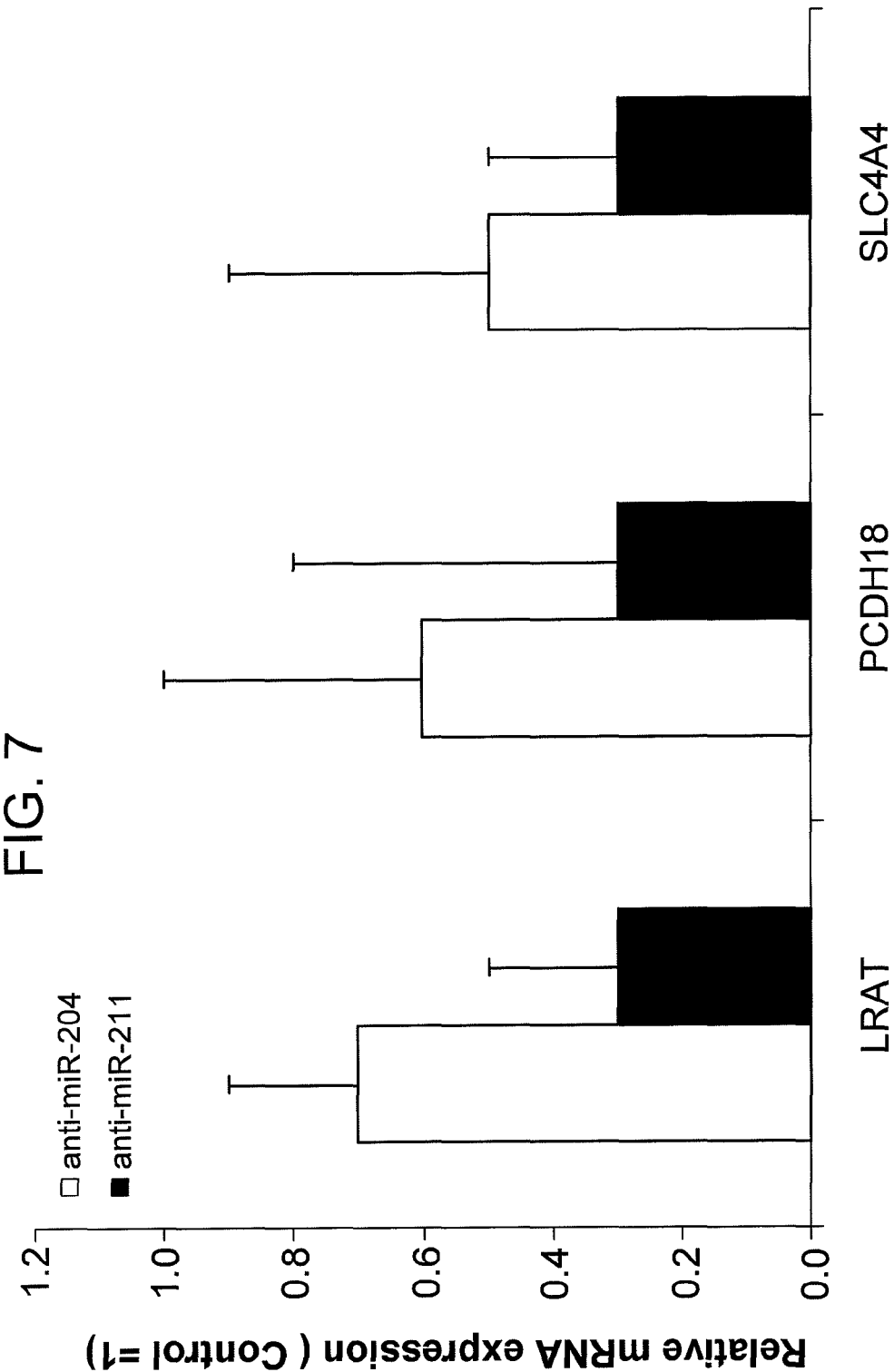
FIG. 7 is a bar graph that shows LRAT, PCDH18, and SLC4A4 are downregulated in anti-miR-204 or anti-miR-211 treated RPE cells.
Figure 8:
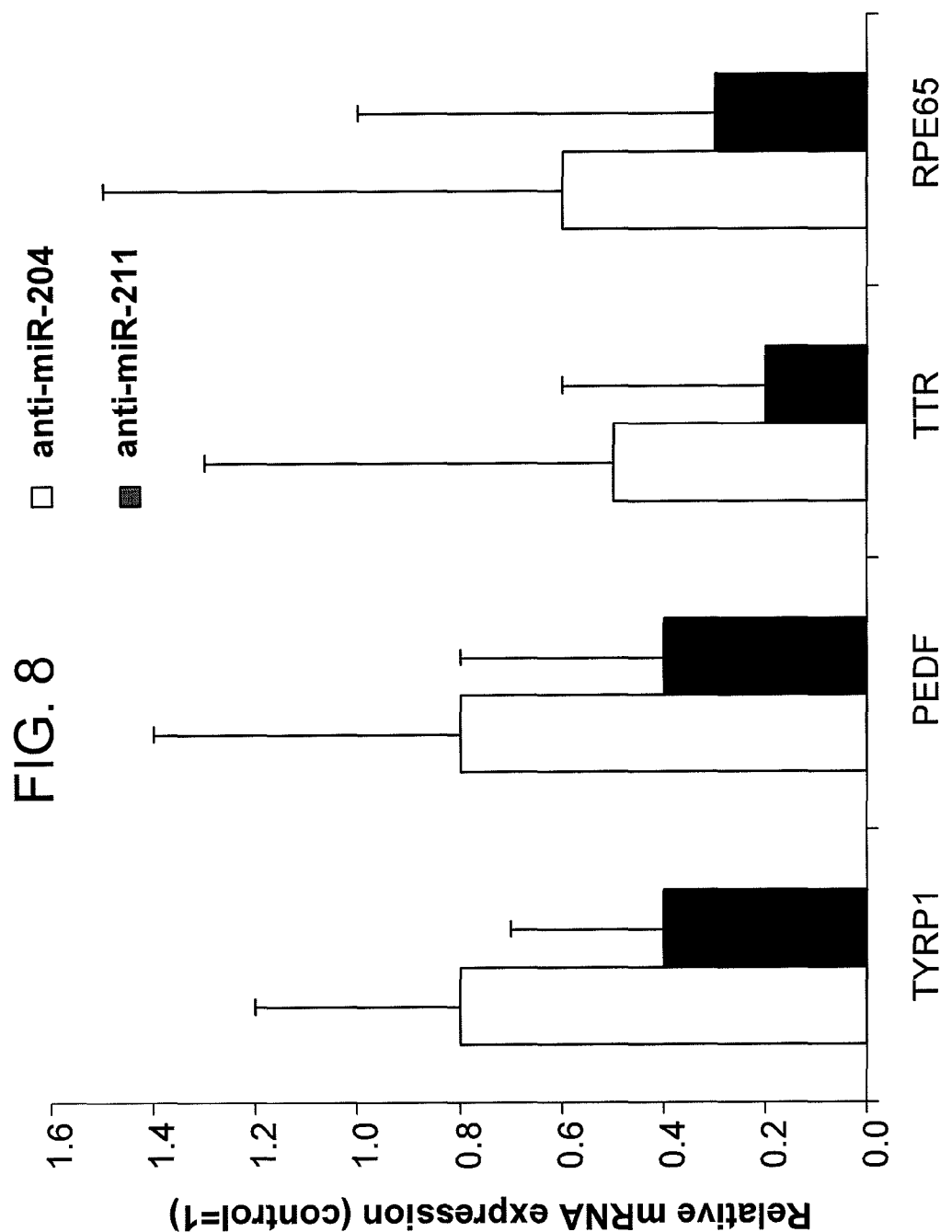
FIG. 8 is a bar graph that shows TYPR1, PEDF, TTR, and RPE65 are downregulated in anti-miR-211 treated RPE cells but not in anti-miR-204 treated RPE cells.

Anti-miR-204 or 211 treatment reduced the expression of several functionally important genes (FIG. 7). LRAT, PCDH18, SLC4A4 participate in visual cycle, junctional complex, and ion transport, respectively. TYRP1, PEDF, TTR and RPE65 are four genes that are known to be associated with melanin synthesis, neuronal protection/angiogenesis, and the visual cycle in native human RPE. FIG. 8 shows that treatment with anti-miR-211 significantly reduces the expression levels of these four genes compared to control; treatment with anti-miR-204 was without effect. TYRP1 expression level is significantly reduced by anti-miR-211 and is one of several genes highly expressed in RPE that is part of the melanin synthesis pathway. ADCY6 and ATF2 are two other highly expressed RPE genes that are in silico targets of miR-204. These two genes are also identified by Ingenuity Pathway Analysis as members of the melanocyte development and pigmentation signaling pathways. Transthyretin, which is critical for vitamin A transport, was decreased by 50-80% on apical and basal baths after treatment with anti-miR-204 or anti-miR-211. Taken together, these results suggest an important regulatory role for miR-204/211 in melanogenesis.

Expression of miR-204/211 decreased in TGFβ treated hfRPE: TGF is known to promote epithelial mesenchymal transition (EMT) in many cell types. Cells that have high TER (after 4-6 weeks in culture) were incubated with TGFβ. No visible morphological changes or changes in TER were observed after 12 days of TGFβ. TGFβ treatments on cells were started before they were confluent. TGFβ1 or TGFβ2 treated cells (in medium with 0.2% FBS or 5% FBS) lost the cuboidal epithelial shape and became more elongated like mesenchymal cells. F-actin staining confirmed that TGFP treated cells lost the cortical ring shape that are typical in epithelial cells and exhibit many elongated stress fibers that have been associated with mesenchymal cells. miR-204 and miR-211 expression are significantly decreased by approximately 45% in cells treated with TGFβ1 using 0.2% FBS medium or 5% FBS medium.

Anti-miR-204/211 decrease TER: Since anti-miRNAs can target and reduce the expression level of specific miRNAs, the effects of these anti-miRNAs were tested on the physiology of fully confluent intact hfRPE monolayers. hfRPE cells with an initial TER of 200 to 1000 $\Omega \cdot cm^2$ were transfected with a mixture of three anti-miRNAs (mi-RNA 204, 211 and 222; 200 nM each) or individual miRNAs (200 nM) and TER was monitored over a period of eight to 12 days. In two different experiments, the anti-miRNA mixture significantly decreased transepithelial electrical resistance by 79±4% (n=3; p<0.005), and 86±2% (n=3; p<0.05), respectively, compared to control (FIG. 9A; Control: Dharmacon anti-miR negative control #2 (5'-UUGUACUACACAAAAGUACUG-3', SEQ ID NO: 6), 600 nM; three anti-miR: anti-miR-204, anti-miR-211, anti-miR-222, 200 nM each. The negative control is a stabilized miRNA based on cel-miR-239b, which has been confirmed to have minimal sequence identity with miRNAs in human, mouse and rat. Cells derived from different tissues were transfected in triplicates for each group in two separate experiments. TER was normalized as percent of average TER for control transfection). For comparison, these cells were treated with either anti-miR 204 or anti-miR 211, and FIG. 9B shows that the anti-miRNA transfection-induced decrease in TER occurs over several days. (Cells were repeatedly transfected with control anti-miR, anti-miR-204, or anti-miR-211 (n=3) every 3 days. Resistance was measured every two days and normalized to control (100%). By six days, cells treated with anti-miR-204 or anti- has significantly lower Rt.) The first noticeable changes in TER occurred at four days. FIG. 9B shows that Control cells have TER at 538±56 $\Omega \cdot cm^2$ while anti-211 treated cells has TER at 257±28 $\Omega \cdot cm^2$ at four days after transfection (p<0.05). The TER for cells treated with anti-miR-204 or 211 was significantly reduced compared to control by 6-8 days (n=3, p<0.05 at day 6 and p<0.05 at day 8).

Figure 9C:
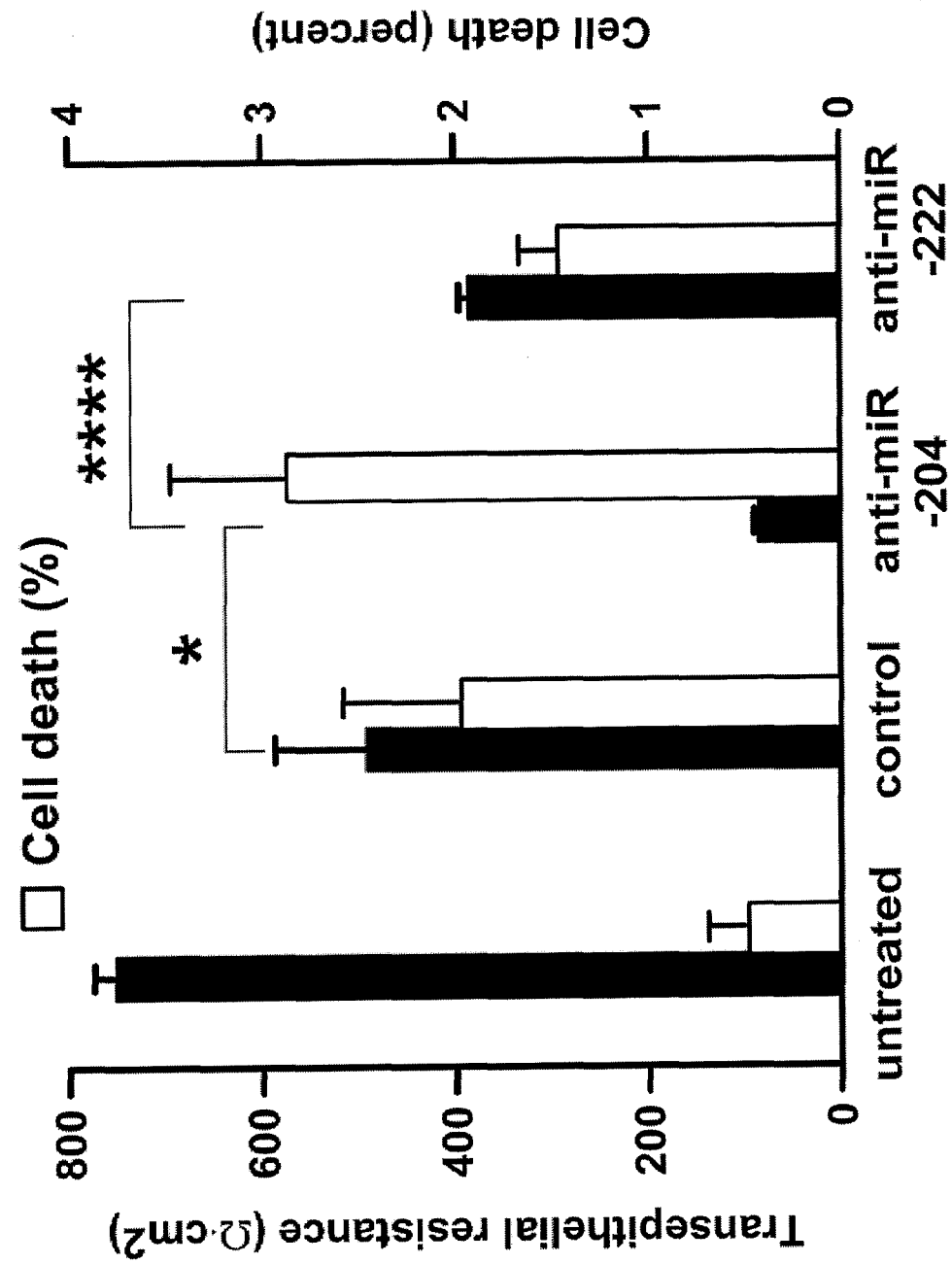
FIG. 9C is a bar graph that shows TER measured after 8 days of transfection. *, p<0.05, **** p<0.001.

FIGS. 9C and D summarize the results from the use of the DharmaFect #4 transfection reagent and anti-miR oligonucleotides. (Cells are untreated or transfected with anti-miR control, anti-miR-204, or anti-miR-222 (n=3, mean±SEM). *, p<0.05, **** p<0.001. Cell death was assessed. Dead cells were counted on the entire transwell and calculated as a percent of total cells (n=3, mean±SEM).) Transfection is repeated every 3-4 days since it is necessary to change medium for a total of 8-12 days with DharmaFect #4 reagent added for the entire time. Dead cells from the entire transwell were counted and the percentage of dead cells was increased by transfection (FIG. 9C, control, anti-miR-204 or anti-miR-222) compared to untreated cells. These data also showed that anti-miR-204 did not significantly increase cell death compared to control or anti-miR-222 treated cells (FIG. 9C). A toxicity titration experiment with TBH was performed to find the percentage of dead cells that is sufficient to decrease TER by 80%. FIG. 9D shows that 3% dead cells (the level seen in anti-miR-204 cells) does not cause a significant decrease in TER while 9% dead cells will induce a 80% decrease in TER. These data suggest that TER decrease in anti-miR-204 treated cells is not due to toxicity of transfection and possibly because of dysfunction of junctional complexes after decreasing miR-204 in the cell.

To further assess the anti-miR-204 induced changes in hfRPE electrophysiology, intracellular microelectrode experiments were performed to analyze the changes in cell membrane voltage and resistance. Electrophysiology was chosen at 8 or 10 days based on the data in FIG. 9B. The data summarized in FIG. 10A shows that after 10 days, TER decreased significantly, from 411±93 $\Omega \cdot cm^2$ in untreated cells (n=6, p<0.05) or 388±67 $\Omega \cdot cm^2$ in anti-miR control treated cells (n=7; p<0.005), to 86±22 $\Omega \cdot cm^2$ in cells treated with anti-miR-204 (n=7). A similar difference was also seen compared to cells treated with an anti-miR control (p<0.005). FIG. 10B shows apical and basolateral membrane potential ($V_A$ and $V_B$) significantly depolarized by approximately 50% in cells treated with anti-miR-204 compared to untreated cells ($p<2\times10^{-13}$) or cells treated with an anti-miR control ($p<2\times10^{-10}$). The ratio of the apical-to-basolateral membrane resistance ($R_A/R_B$) increased in anti-miR-204 treated cells (n=31) by 35% and 156%, compared to anti-miR control (n=29, $p<3\times10^{-5}$) or untreated cells (n=28, $p<1\times10^{-13}$), respectively.

Anti-miR-204/211 affects epithelial differentiation: Treatment with anti-miR 204/211 significantly increased expression of JUN/FOS, SNAI1, SNAI2 and SMAD3 (FIG. 5), and therefore the anti-miR 204/211 induced decreases in TER are possibly mediated by this increase in transcription factor expression. It was hypothesized that transcription factor blockade in the presence of anti-miR 204/211 would prevent or rescue the decrease in TER. FIG. 11A shows that blocking transcription factors rescue anti-miR induced decrease in transepithelial electrical resistance. Cultured human fetal RPE cells were transfected with anti-miR or anti-miR plus siRNA for specific genes. Transepithelial resistance was measured on the first and last day during the experiments. Cells treated with a combination of JUN/FOS siRNA and anti-miR-204/211 did not significantly differ in TER compared to cells treated with anti-miR-204 or anti-miR-211 alone. In contrast, cells treated with a combination of SNAI1, SNAI2 and SMAD3 siRNA and anti-miR-204/211 completely rescued TER relative to control (FIG. 11B).

Claudin-19 siRNA significantly decreases TER: Claudin-19 is a junctional protein and is the most highly expressed claudin in hfRPE. Claudin-19 is a predicted target for several transcription factors, including Snail1, which is known to down-regulate expression of junctional proteins, including E-cadherins, claudins, 3, 4, 7, and occludin. It was examined if lower Caudin-19 expression is associated with lower TER since anti-miR-204/211 decreased TER, CLDN-19 expression and increased expression of clauidn-19 suppressors, such as SNAI1 and SNAI2. FIG. 12A shows that claudin-19 siRNA caused a significant decrease in TER at concentrations at 20 or 50 nM. TER decreased by 50% at 2 days and by 90% at 8 days after siRNA transfection. Data in FIG. 12B confirmed that claudin-19 mRNA decreased by 65% at two days after claudin-19 siRNA transfection. These data confirmed that decreased Claudin-19 expression by siRNA caused a significant reduction in TER.

Discussion

Using Taqman Q PCR profiling, eight miRNAs (miR-184, 187, 200a, 200b, 204, 211, 221, 222) have been identified that are enriched (>10 fold, p<0.05) in human fetal RPE. Five of six miRNAs are also significantly higher in RPE than in a panel of 20 tissues distributed throughout the body. Expression for miR-204 or 211 is significantly lower in NCI panel of 60 tumor cell lines than normal tissue (n=29). Anti-miR 204 or 211 treatment significantly upregulated many genes that help regulate proliferation/migration (JUN, SNAI1, SNAI2, SMAD3, PDGFA, PDGFRA), and downregulated many RPE specific genes, such as LRAT, TYRP1, PEDF, TTR, RPE65, Claudin-19. Anti-miR-204/211 decreased TER and caused apical and basolateral membrane potential depolarization. Anti-miR-204/211 induced TER decrease is blocked by siRNA mixtures against SNAI1, SNAI2, and SMAD3.

siRNA against Claudin-19 inhibited Claudin-19 expression and caused significant decrease in TER. These data suggest that miR-204/211 regulates epithelial junctions and could be a candidate tumor suppressor and important in epithelial differentiation.

Expression and Function of miR-204/211: miR-204 is expressed in all 20 adult human tissues and is relatively high in brain and kidney. miR-204/211 are identified as enriched in the mouse eye by comparing to other 12 regions of brain by at least three fold. miR-204 has been detected using in-situ hybridization as only in RPE at E10.5 and expands into neuroretina at later stages. It was also detected in choroid plexus E14.5, which shares embryonic origin with RPE and was suggested to contribute to the differentiation of RPE and neuroretina from their common precursors. RPE has higher expression for miR-204 than any of the 20 tissues. The estimated copy number for miR-204 is approximately 10,000 per cell. This is similar to the report of highest miR (miR-16) in five tissues (4000 to 30,000 copies per cell).

miR-204 and miR-211 share the same seeding region sequence and only differ by two nucleotides in the 3' region. They were classified as one family with the same set of predicted targets. Without being bound to any theory, miR-204/211 belong to the same family and share the same seed matching region, yet their tissue specificity is very different, indicating that they have different targets or their effect on a given target requires other miRNA/cell specific factors. In the RPE, miR-211 is expressed at a high level and could overlap with miR-204 function. In most other tissues, miR-211 is expressed at a very low level and is unlikely to affect miR-204 function. In melanocyte, miR-211 is expressed at higher level than miR-204, indicating that miR-211 has a more dominant function than miR-204. Only miR-211 expression is significantly lower in melanoma than melanocyte while miR-204 did not change significantly. RPE and melanocyte are the only two types of cells in the body that is capable to produce melanin pigments. These two cell types also have high miR-211 expression level, indicating that miR-211 could be involved in regulating melanogenesis.

Expression and function of miR-200 family: Higher expression of miR 200a/b/c has been detected in olfactory bulb epithelium compared to other 12 regions of brain. Although miR-200a is considered as enriched in RPE by comparison to retina and choroid, miR-200a expression in hfRPE is not significantly different when compared to the 20-tissue panel. Among the RPE enriched miRNAs, miR-200 family (miR-200a and b) has been shown to regulate EMT by targeting ZEB1 and ZEB2. These two transcription factors, together with SNAI1, SNAI2, E47 and TWIST, have been identified as inducer of EMT and important in tumor invasion and metastasis. Inhibition of miR-200 family induced EMT while overexpression of miR-200 promotes mesenchymal to epithelial transition (MET).

Expression and function of miR-221/222: Expression of 221/222 is high in hippocampus in comparison to other 12 regions in the brain. It has been shown that overexpression of miR-221/222 downregulates c-kit in human umbilical vein endothelial cells and CD34+ erythropoietic progenitor cells. MiR-221/222 is overexpressed in human thyroid papillary carcinomas with a dramatic loss of c-kit transcript and protein. miR-221 and 222 also affects the proliferation potential of human prostate carcinoma cell lines by targeting tumor suppressor p27 Kip1. miR-222 expression is significantly higher in tumor than normal tissue, suggesting that miR-221/222 is a potential oncogenic miRNA.

miRNAs identified in this experiment are corroborated by expression patterns identified with microarray and in situ hybridization. Three out of five retina enriched miRNAs (miR-96/182/183) were identified by microarray in mouse retina and also detected as enriched in mouse eye by comparing to other 12 regions of brain by at least three fold. MiR-182/183 were shown to be expressed in mouse retina by in situ hybridization. Expression for miR-96 and miR-183 increased by more than three fold in the retina of a mouse model of retinitis pigmentosa compared to normal neuroretina. This mouse model of retinitis pigmentosa has similar phenotype to human counter part and now has similar miR expression, indicating that these miRNAs could also be involved in human retinitis pigmentosa.

The other three novel neuroretina enriched miRNAs (miR-124a, 124b and 135) have been identified as brain enriched miRNAs and miR-135 expression is limited to brain. miR-124 has been shown to promote neuronal differentiation. After removing Dicer from mouse retina using conditional knockout technique, mature miR-96 and miR-124a were found to be decreased by 70% compared with wild type at 3 months while the animal lost response to light and developed retinal degeneration. These data suggest that these neuroretina enriched miRNAs could be important in neuroretina development and photoreceptor differentiation.

Functions of choroid enriched miRNAs: miR-146a and miR-155 have been shown to be involved in the immune response. LPS stimulation of a mouse macrophage cell line (Raw 264.7) and LPS injection in C57BL/6 mice resulted in the up-regulation of miR-155. After 30 min of TNF-α stimulation, the level of miR-155 decreased but recovered after treating for one hour. Human monocytes treated with LPS and to virally relevant stimuli showed the up-regulation of the miR-155 level. The B cells from miR-155 knockout mice showed an impaired response toward LPS. miRNA-155 likely plays a role in the function of the immune system. Cytokine cocktail (TNF-α, IL-1β, and IFN-γ) treatment significantly upregulated miR-146a and 155 expression, suggesting RPE has a fundamental role in response to bacterial and viral infection.

miR-204/211 and TRPM3/TRPM1: Anti-miR-204/211 caused a decrease in TER. TER decrease could be mediated by cellular pathways or paracellular pathway. In paracellular pathway, anti-miR could decrease resistance by disrupting junctional complexes. miR-204 and miR-211 are located in the intron region of transient receptor potential subfamily M member 3 (TRPM3) and member 1 (TRPM1), respectively. TRPM are cation channels and are known as tumor suppressors. Decreased level of TRPM is associated with increased tumor invasiveness. TRPM3 also has predicted binding site for miR-204/211. Without being bound to theory, it is possible that TRPM3 is upregulated when cells are treated anti-miR-204/211, which relief miR mediated inhibition. Intronic miRNA and its host gene also could be regulated independently if intronic miRNA has its own independent transcription unit. MITF is important transcription factor for TRPM1/TRPM 3 expression. miR-204/211 might regulate TRPM3/TRPM1 expression.

miR-204/211 is a potential tumor suppressor: Both Snail 1 and Slug has binding predicted sites for miR 204 and miR 211. This is consistent with the hypothesis that miR-204 or miR-211 directly inhibits Snail and Slug and anti-miR 204/211 increase expression of Snail 1 and Slug. Snail1 and slug are known to upregulated in EMT and in tumor invasion. MiR-204 expression is significantly lower in tumor than in normal tissue. Anti-miR-204 decreased miR-204 inside cell and mimic the tumor cells. Cells transfected with anti-miR-204/211 display a decreased TER and other markers mimic tumor invasion. MiR-204 potential serves as a tumor suppressor by promote cell differentiation.

Transcriptional repressor Snail1 downregulates the expression of Claudin-3, 4 and 7 in Eph4 epithelial cells and Cldn1 in MDCK cells during EMT. Claudin-19 has three predicted poorly conserved binding sites for miR-204/211. Snail1 might regulate Claudin-19 expression. In anti-miR-204/211 treated cells, Snail1 mRNA expression increased and protein is translocated into nucleus and activated. Active Snail1 decreased expression of claudin-19 or other claudins E-Cadherins, or occludins and decreased TER, triggered an EMT like process.

miR-204/211 is important in epithelial differentiation and physiological function: Epithelial-Mesenchymal transition is a fundamental important process during embryogenesis. EMT is also involved in many pathological conditions, such as fibrosis and tumor metastasis. EMT could be triggered by several extracellular signals, such as TGFb, FGF and EGF. TGFb signaling pathways in EMT has been extensively studied. TGFb triggers EMT through either SMAD depend pathway (SMAD2/3) or SMAD independent protein kinase to induce JUN/Fos and form AP-1. AP-1 is required for TGFb induced EMT in human keratinocytes and upregulate Snail expression.

Since EMT is important in metastasis of many epithelial tumors, it is important to understand the function of miR in tumor metastasis. Snail and slug have been shown to be critical in many tumor metastases. Snail is a transcription factor expressed during epithelial-to-mesenchymal transition, and it downregulates expression of junctional proteins, including E-cadherins, claudins, 3, 4, 7, and occludin. Both Snail1 and Snail2 have been shown to inhibit Claudin 1 expression in MDCK cells. Overexpression of these two factors abolished the total tissue resistance in MDCK cells. It is possible that the functions of miR-204/211 or similar miR discovered in these retinal pigment epithelial cells could be exist in other epithelial cells. It is possible to inhibit the EMT process by increasing the miR level in the cell and prevent tumor metastasis.

TGFb has been known to trigger EMT. In keratinocytes, expression of miR-211 and three other miRNAs were decreased after 5 hours of TGFb treatment. Expression for c-fos increased by 34 fold while MITF was decreased by three fold after 4 hours of TGFb treatment. When RPE was transfected with miR-204 or miR-211, the expression level was decreased by 80%. This finding confirmed that decreasing levels of miR-204/211 is accompanying the EMT. It suggests that increasing levels of miR-204/211 is likely associated with the reverse of EMT, i.e., differentiation of epithelial cells.

In SMAD dependent pathway, SMAD3 is required for TGFb induced EMT. SMAD3 has been shown to upregulate Snail. Snail1 and Snail2 are known to be critical in EMT. Expression for SNAIL1 SNAIL2 and SMAD3 are increased when cells are treated with anti-miR-204 or 211. Transfection of siRNA against SMAD3, SNAIL1 or SNAIl2 individually did not rescue the TER decrease induced by anti-miR 204/211. However, mixture of three siRNA always prevents the TER decreased caused by anti-miR-204/211 (at least four biological repeats).

PDGF-A and PDGF receptors increased in TGF-b induced EMT. This data shows the anti-miR 204/211 increased PDGF-A and PDGFRB expression by 10 fold and three fold, respectively. This is another indicator that anti-miR-204/211 triggered EMT like process in RPE. In PVR, RPE dedifferentiate and undergo epithelial-mesenchymal transition in response to PDGF and VEGF signaling.

Specialized function of RPE includes enzymes for visual cycle and pigmentation. When cells are treated with anti-miR-204 or 211, expression for many of these enzymes decreased, such as LRAT, RPE65, suggesting that RPE are shutting genes expressed after cell differentiation. This is another indicator that cells are undergoing de-differentiation. It is also significant that miRNA can modulate many key enzymes that are very important in maintaining visual function.

The data shows that anti-miR 204 or 211 induced a significant decrease (80%) of total transepithelial resistance (TER or RT) and apical and basolateral membrane depolarization. The later effect could be caused by changes in any electrogenic mechanism, such as potassium channels. Mir-204/211 has four predicted targets that are part of potassium channel family (KCNA3, KCNJ1, KCNMA1, and KCTD1). Total transepithelial resistance (RT) has two parallel components, cellular and paracellular: the cellular path has two components made up of the apical (RA) and basolateral membrane resistance (RB). The paracellular path resistance is denoted by RS. Simple equivalent circuit analysis shows that the relation between RT, RS, RA, and RB is given as follows: 1/RT=1/RS+1/[RA+RB]. Previously it was demonstrated in mammalian RPE that [RA+RB] is approximately 8-fold larger than RS and a similar result has been demonstrated for cultured human fetal RPE (25-fold). This experimental result means that RT is mainly determined by RS and that an 80% reduction in RT reflects, to within 10%, an 80% reduction in paracellular path resistance (RS). The tight junction proteins are what determine the paracellular path resistance and therefore these experiments provide strong physiological evidence for the conclusion that miRNAs 204 and 211 affect the integrity of tight junctions.

EXAMPLE 2

This example demonstrates that loss of miR-204 in a knockout (KO) mouse results in detrimental effects on the eye in vivo.

Methods

The stem loop sequence of the mouse pre-miR-204 (5'-TGGACTTCCCTTTGTCATCCTATGCCT-GAGAATATATGAAGGAGGCTGGGAAGGCAA AGG-GACGTTCA-3'; SEQ ID NO: 7) was downloaded from miRBase at the Welcome Trust Sanger Institute and plugged into the "blat" program at the University of California Santa Cruz genome browser for genomic localization. The sequence is perfectly matched to a region in chromosome 19 (chr19:22,825,095-22,825,162), and it is located within the 6th intron of the Trpm 3 gene. A BAC clone of 129sv origin covering the genomic locus was obtained from the Welcome Trust Sagner Institute and used in making a targeting construct by recombinant technology (Zhang et al., Nature Biotechnology, 18:1314-1317 (2000)). The targeting strategy was aimed at replacing the entire stem loop sequence of miR-204 with a $Neo^R$ cassette to achieve a deletion of the entire coding sequence (FIG. 13). After electroporation of mouse embryonic stem (ES) cells with the targeting construct, homologous recombination events were screened first by long range PCR and then confirmed by Southern blotting. A total of 20 correctly targeted ES clones were identified, three of which were further characterized by karyotyping. High percentage chimeras were obtained from microinjections and further bred for germline transmission. F1 aguti individuals were screened for the presence of the targeted allele by long range PCR, followed by Southern blotting using the same probes as used in ES clone screening. Heterozygous F2 mice were further bred with C57 wild-type mice. The knockout allele was brought to homozygosity by intercrossing of the heterozygous individuals, and proved not to be embryonic lethal, as the inheritance of the knockout allele showed a Mendelian pattern.

Results

Preliminary experiments show that defects exist in the retina and lens of the mice homozygous for miR-204 knock out, with a reduction in electroretinogram (ERG) amplitude. In particular, the photoreceptor a-wave is reduced by 50%. The reduction in a-wave amplitude, which originates in the distal retina (photoreceptor outer segments), shows that there is a functional deficiency in RPE-photoreceptor interactions, probably caused by a loss of RPE tight junction integrity. Because miR-204 is only expressed in RPE and not in retina, this indicates that any photoreceptor or retinal defects in the miR-204 knock-out model must have originated in the RPE.

Additionally, the miR-204 KO model may have relevance to brain tissue, for example, the choroid plexus, which like the RPE, is derived from neuroectoderm.

All references, including publications, patent applications, and patents, cited herein are hereby incorporated by reference to the same extent as if each reference were individually and specifically indicated to be incorporated by reference and were set forth in its entirety herein.

The use of the terms "a" and "an" and "the" and similar referents in the context of describing embodiments of the invention (especially in the context of the following claims) are to be construed to cover both the singular and the plural, unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate certain embodiments of the invention and does not pose a limitation on the scope of the invention unless otherwise claimed. No language in the specification should be construed as indicating any non-claimed element as essential to the practice of any embodiments of the invention.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

What is claimed is:

1. A pharmaceutical composition comprising substantially purified miR 204, substantially purified siRNA for SNAIL1, substantially purified siRNA for SNAIL2, and substantially purified siRNA for SMAD3, and a pharmaceutically acceptable carrier.

2. A method of treating detrimental epithelial cell proliferation or loss of epithelial cell differentiation in an individual, comprising administering an effective amount of the pharmaceutical composition of claim 1 to the individual.

3. A method of treating age-related macular degeneration or proliferative vitreal retinopathy in an individual, comprising administering an effective amount of the pharmaceutical composition of claim 1 to the individual.

4. A method of facilitating the transport of a substance across an epithelium in an individual, comprising administering an effective amount of the pharmaceutical composition of claim 1 to the individual.

5. The method of claim 2, wherein the epithelial cell is a retinal pigment epithelial cell.

6. The method of claim 4, wherein the epithelium is retinal pigment epithelium.

7. The method of claim 2, wherein the individual is a mammal.

8. The method of claim 3, wherein the individual is a mammal.

9. The method of claim 4, wherein the individual is a mammal.

10. The method of claim 7, wherein the mammal is a human.

11. The method of claim 8, wherein the mammal is a human.

12. The method of claim 9, wherein the mammal is a human.

13. A pharmaceutical composition comprising:
(a) substantially purified miR 204;
(b) substantially purified siRNA for
 (i) ROCK1,
 (ii) ROCK2,
 (iii) RHOB, or
 (iv) any combination of (i), (ii), and/or (iii); and
(c) a pharmaceutically acceptable carrier.

14. A pharmaceutical composition comprising:
(a) substantially purified miR 204;
(b) substantially purified
 (i) anti-miR 221,
 (ii) anti-miR 222, or
 (iii) a combination of (i) and (ii); and
(c) a pharmaceutically acceptable carrier.

15. A pharmaceutical composition comprising:
(a) substantially purified miR 204;
(b) substantially purified siRNA for
 (i) PDGFA,
 (ii) PDGFRB, or
 (iii) a combination of (i) and (ii); and
(c) a pharmaceutically acceptable carrier.

16. A pharmaceutical composition comprising substantially purified miR 204, a TGFβ receptor antagonist, and a pharmaceutically acceptable carrier.

* * * * *